United States Patent
Kondou

(10) Patent No.: US 9,248,451 B2
(45) Date of Patent: Feb. 2, 2016

(54) SAMPLE ANALYZER COMPRISING A REAGENT CONTAINER HOLDER

(75) Inventor: Keitarou Kondou, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 241 days.

(21) Appl. No.: 12/605,834

(22) Filed: Oct. 26, 2009

(65) Prior Publication Data

US 2010/0104478 A1   Apr. 29, 2010

(30) Foreign Application Priority Data

Oct. 27, 2008   (JP) ................................. 2008-275917

(51) Int. Cl.
| | | |
|---|---|---|
| G01N 35/10 | (2006.01) | |
| B01L 9/00 | (2006.01) | |
| B01L 3/00 | (2006.01) | |
| G01N 35/00 | (2006.01) | |
| G01N 35/02 | (2006.01) | |

(52) U.S. Cl.
CPC . *B01L 9/00* (2013.01); *B01L 3/527* (2013.01); *G01N 35/00663* (2013.01); *G01N 35/00732* (2013.01); *B01L 2200/143* (2013.01); *B01L 2300/021* (2013.01); *B01L 2300/0803* (2013.01); *B01L 2300/18* (2013.01); *G01N 35/0095* (2013.01); *G01N 35/025* (2013.01); *G01N 35/1016* (2013.01); *G01N 2035/00217* (2013.01); *G01N 2035/1025* (2013.01)

(58) Field of Classification Search
CPC ................. G01N 35/00663; G01N 2035/1025
See application file for complete search history.

(56) References Cited

U.S. PATENT DOCUMENTS

| | | | |
|---|---|---|---|
| 4,451,433 A | 5/1984 | Yamashita et al. | |
| 4,754,414 A | 6/1988 | Gocho | |
| 5,428,993 A * | 7/1995 | Kobashi | 73/149 |
| 5,719,059 A * | 2/1998 | Mimura et al. | 436/50 |
| 5,730,939 A | 3/1998 | Kurumada et al. | |
| 2004/0091396 A1* | 5/2004 | Nakamura et al. | 422/65 |
| 2005/0123445 A1* | 6/2005 | Blecka et al. | 422/64 |
| 2008/0063570 A1 | 3/2008 | Fujino et al. | |

FOREIGN PATENT DOCUMENTS

| | | |
|---|---|---|
| EP | 0510686 A2 | 10/1992 |
| EP | 1 422 528 A2 | 5/2004 |
| JP | 61-212767 | 9/1986 |
| JP | H4-326063 A | 11/1992 |
| JP | H7-23895 B | 3/1995 |
| JP | 09-127123 | 5/1997 |
| JP | 2000-266758 | 9/2000 |
| JP | 2000-346851 | 12/2000 |

* cited by examiner

*Primary Examiner* — P. Kathryn Wright
(74) *Attorney, Agent, or Firm* — Sughrue Mion, PLLC

(57) ABSTRACT

The present invention is to present a sample analyzer comprising: a reagent container holder for holding a reagent container for containing a reagent to be used for analyzing a sample; a measurement unit for measuring a value representing an amount of the reagent in the reagent container held by the reagent container holder; an instruction receiver for receiving an instruction to obtain a remaining amount of the reagent in the reagent container; a measurement controller for controlling the measurement unit so as to measure the value representing the amount of the reagent in the reagent container, when the instruction receiver has received the instruction; and a remaining reagent amount obtainer for obtaining remaining reagent amount information indicating the remaining amount of the reagent in the reagent container, based on a measurement result by the measurement unit.

15 Claims, 26 Drawing Sheets

F I G. 6
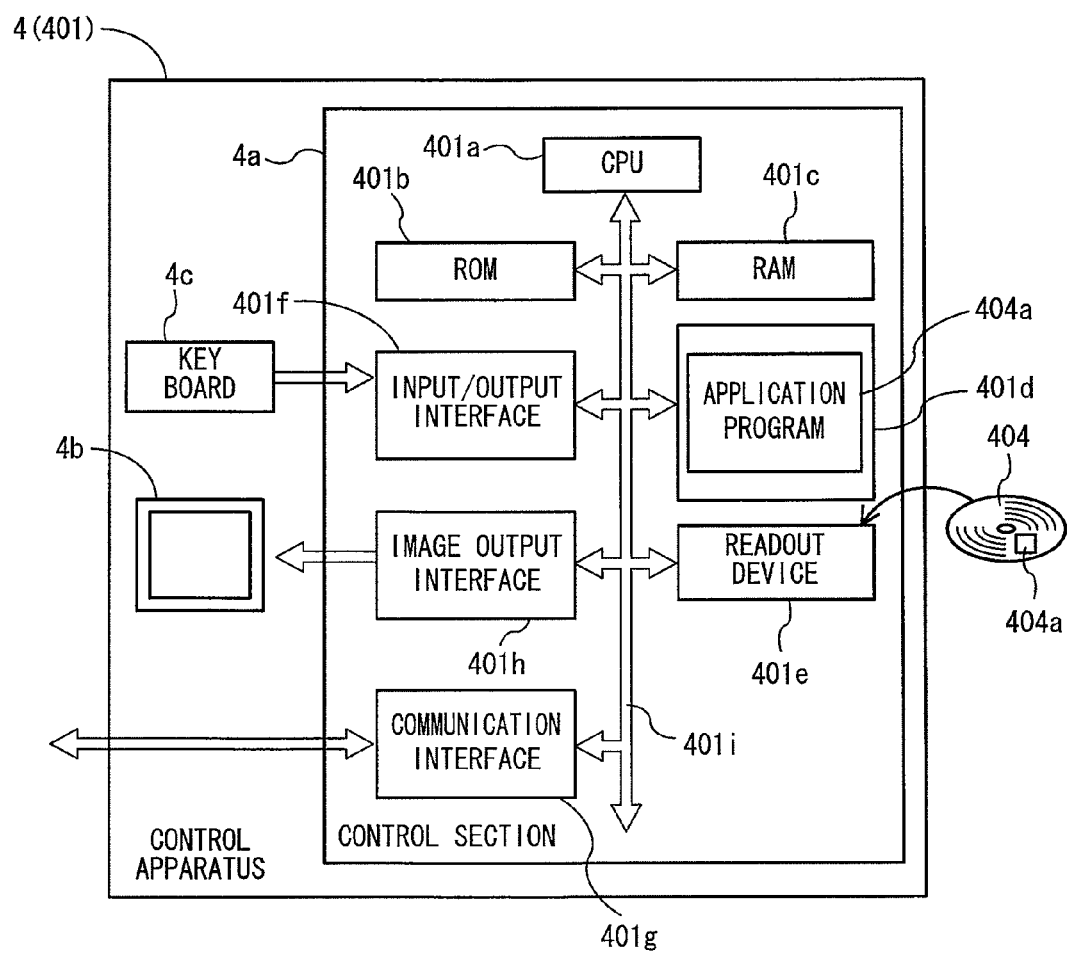

F I G. 1 2
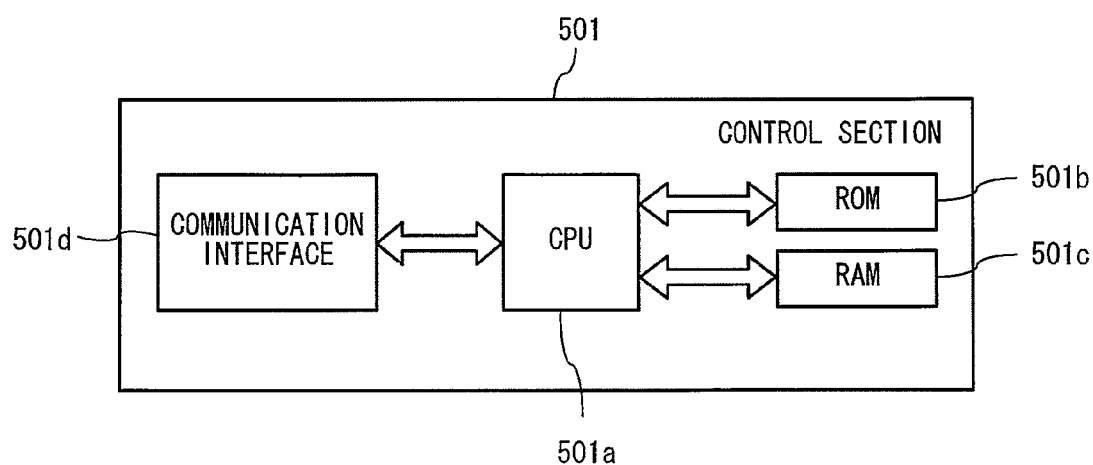

FIG. 19

| | REAGENT IDENTIFICATION INFORMATION | | | | | REMAINING REAGENT AMOUNT INFORMATION | |
|---|---|---|---|---|---|---|---|
| HOLDER No. | REAGENT NAME | LOT No. | CONTAINER TYPE | EXPIRATION DATE | ... | USABLE AMOUNT | NUMBER OF REMAINING TESTS |
| A1-1 | ○× | ○△× | △ | 2008/10/30 | ... | 1.2mL | 6 |
| A1-2 | ○△ | △×○ | × | 2008/10/5 | ... | 0mL | 0 |

36

SAMPLE ANALYZER COMPRISING A REAGENT CONTAINER HOLDER

FIELD OF THE INVENTION

The present invention relates to a sample analyzer, and particularly to a sample analyzer capable of displaying remaining amount information of a reagent to be used in analysis.

BACKGROUND

Conventionally, U.S. Patent Publication No. 2008/0063570 discloses a sample analyzer for analyzing components in a sample by measuring a measurement specimen prepared from the sample and a reagent. In the sample analyzer described in U.S. Patent Publication No. 2008/0063570, a plurality of reagent containers are held in a reagent holding section, and a reagent aspirating pipette is inserted into the reagent containers to aspirate reagents therefrom. Every time a reagent aspirating operation by the reagent aspirating pipette is performed, the sample analyzer detects a liquid level in a reagent container by using a liquid level sensor provided at the tip of the reagent aspirating pipette, so as to determine whether or not a necessary amount of reagent for preparing a measurement specimen is remaining in the reagent container. Based on the detection result, the remaining amount of the reagent to be aspirated is obtained. If the remaining amount of the reagent is less than a predetermined amount, a warning is displayed on a display section of a control apparatus such as a personal computer that is provided to the sample analyzer.

However, in the sample analyzer described in U.S. Patent Publication No. 2008/0063570, in order to reduce time necessary for the sample analyzer to be in a measurement standby state, the liquid level detection operation is not performed before the measurement is performed. The liquid level detection operation is performed when aspirating a reagent, and the remaining amount of the reagent is calculated. For this reason, there is a case where insufficiency of the remaining amount of the reagent in the reagent container held in the reagent holding section is recognized only after a measurement operation is started and the operation to aspirate the reagent is performed. In the case where insufficiency of the remaining amount of the reagent is recognized after the start of the measurement, the user needs to search, at the time, a refrigerator or the like for a necessary reagent and set the reagent in the sample analyzer. However, the reagents to be used in the analysis include a reagent which is stored in a frozen state and defrosted before use or a reagent which is used after dissolving freeze-dried reagent powder in purified water. Therefore, in the above conventional sample analyzer, there is a case where it takes time to replace the reagents and restart the measurement.

SUMMARY

A first aspect of the present invention is a sample analyzer comprising:
a reagent container holder for holding a reagent container for containing a reagent to be used for analyzing a sample;
a measurement unit for measuring a value representing an amount of the reagent in the reagent container held by the reagent container holder;
an instruction receiver for receiving an instruction to obtain a remaining amount of the reagent in the reagent container;
a measurement controller for controlling the measurement unit so as to measure the value representing the amount of the reagent in the reagent container, when the instruction receiver has received the instruction; and
a remaining reagent amount obtainer for obtaining remaining reagent amount information indicating the remaining amount of the reagent in the reagent container, based on a measurement result by the measurement unit.

A second aspect of the present invention is a sample analyzer comprising:
a reagent container holder for holding a reagent container for containing a reagent to be used for analyzing a sample;
an identification information obtainer for obtaining identification information that identifies the reagent container held by the reagent container holder;
a measurement unit for measuring a value representing an amount of the reagent in the reagent container held by the reagent container holder;
a measurement controller for controlling the measurement unit so as to measure the value representing the amount of the reagent in the reagent container, when the identification information obtainer has obtained the identification information of the reagent container; and
a remaining reagent amount obtainer for obtaining remaining reagent amount information indicating a remaining amount of the reagent in the reagent container, based on a measurement result by the measurement unit.

A third aspect of the present invention is a sample analyzer comprising:
a reagent container holder for holding a reagent container for containing a reagent to be used for analyzing a sample;
a measurement unit for measuring a value representing an amount of the reagent in the reagent container held by the reagent container holder;
a measurement controller for automatically controlling the measurement unit so as to measure the value representing the amount of the reagent in the reagent container held by the reagent container holder, when the sample analyzer has started up; and
a remaining reagent amount obtainer for obtaining remaining reagent amount information indicating a remaining amount of the reagent in the reagent container, based on a measurement result by the measurement unit.

BRIEF DESCRIPTION OF THE DRAWINGS

FIG. 6 is a block diagram showing a control apparatus of the sample analyzer shown in FIG. 1.

FIG. 12 is a block diagram showing a control section of the measurement mechanism section of the sample analyzer shown in FIG. 1;

FIG. 19 is a schematic diagram showing a configuration of a reagent information database;

FIG. 23 is a flowchart illustrating a process of deleting, by a user, remaining reagent amount information about a reagent container from a hard disk 401d of a control section 4a;

DETAILED DESCRIPTION OF THE EMBODIMENT

Hereinafter, an embodiment of a sample analyzer of the present invention will be described in detail with reference to the attached drawings.

[Overall Configuration of the Sample Analyzer]

A sample analyzer 1 is an apparatus for optically measuring and analyzing the quantity and degree of activity of a specific substance related to coagulative and fibrinolytic functions of blood. Here, the sample analyzer 1 uses plasma as a sample. The sample analyzer 1 according to the present embodiment optically measures the sample by using a coagulation time method, synthetic substrate method, and immunonephelometry. The coagulation time method used in the present embodiment is a measurement method for detecting a coagulation process of the sample through changes observed in transmitted light. Here, measurement items are PT (prothrombin time), APTT (activated partial thromboplastin time), Fbg (fibrinogen quantity), and the like. Also, measurement items for the synthetic substrate method include AT III and the like, and measurement items for the immunonephelometry include D-dimer, FDP and the like.

Figure 1:
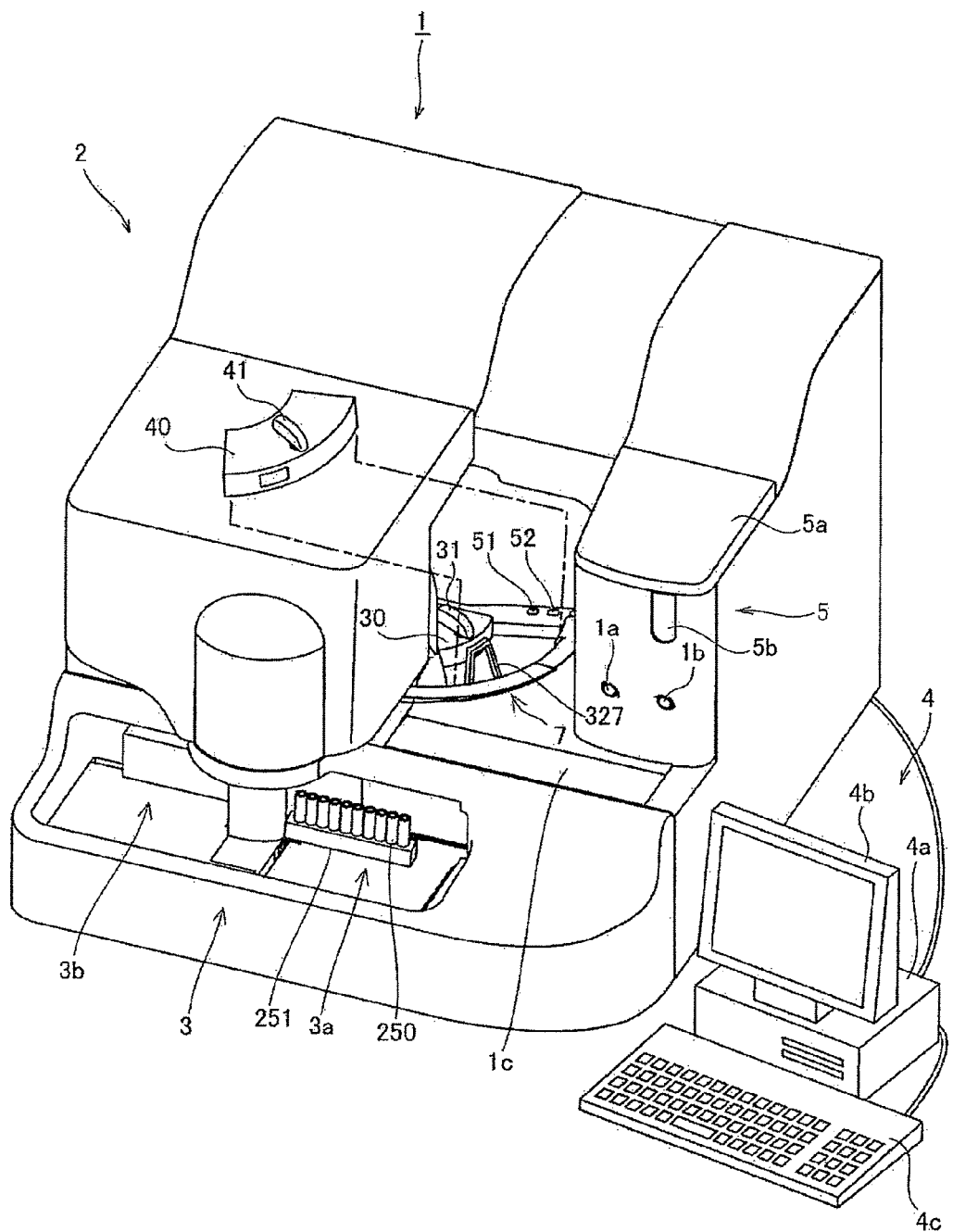
FIG. 1 is a perspective view showing an overall structure of an embodiment of a sample analyzer of the present invention.
Figure 2:
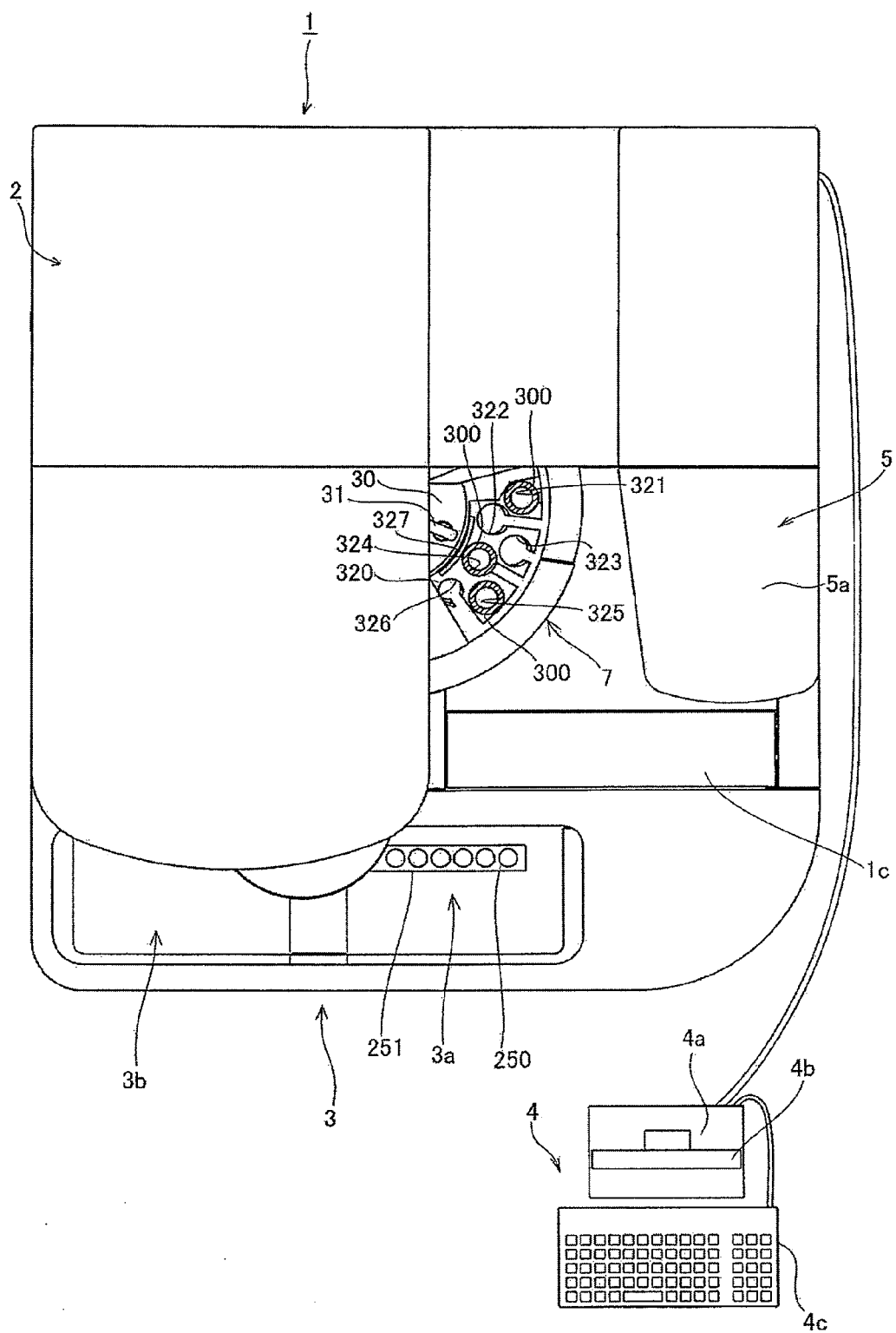
FIG. 2 is a plane view of the sample analyzer shown in FIG. 1.

As shown in FIGS. 1 and 2, the sample analyzer 1 includes a measurement mechanism section 2, a transport mechanism section 3 positioned in front of the measurement mechanism section 2, and a control apparatus 4 electrically connected to the measurement mechanism section 2. The measurement mechanism section 2 is provided with a cuvette feeding section 5 into which cuvettes 200 (see FIG. 4), which are containers of samples used in the measurement, are fed. The cuvette feeding section 5 is provided with a cover 5a that can be opened/closed and a window 5b through which the inside of the cuvette feeding section 5 can be visually observed. Further, on the front side of the cuvette feeding section 5, an emergency stop button 1a and a measurement start button 1b are provided. The cover 5a (see FIG. 1) is provided for allowing the cuvettes 200 to be fed into a first hopper 161a (see FIG. 4) of a below-described cuvette supply mechanism section 160. A user can visually recognize, through the window 5b, the remaining number of cuvettes 200 stored in the first hopper 161a (see FIG. 4). The emergency stop button 1a (see FIG. 1) has a function to stop the measurement in case of emergency. The measurement start button 1b (see FIG. 1) is configured such that the measurement is started by pressing the measurement start button 1b. This allows the user to immediately start the measurement after feeding the cuvettes 200. Note that, the measurement can also be started or stopped by operating the control apparatus 4.

The control apparatus 4 is structured as a personal computer (PC) 401 or the like. As shown in FIGS. 1 and 2, the control apparatus 4 includes a control section 4a, a display section 4b, and a keyboard 4c. The control section 4a has a function to transmit, to a below-described control section 501 of the measurement mechanism section 2, an operation start signal for starting the operation of the measurement mechanism section 2, and has a function to analyze optical information about a sample, which is obtained by the measurement mechanism section 2. The control section 4a includes a CPU, ROM, RAM and the like. The display section 4b is provided so as to display information about interference substances existing in the sample (hemoglobin, chyle (lipid), and bilirubin), and display analysis results obtained by the control section 4a.

Next, a configuration of the control apparatus 4 will be described in detail. As shown in FIG. 6, main components of the control section 4a are a CPU 401a, a ROM 401b, a RAM 401c, a hard disk 401d, a readout device 401e, an input/output interface 401f, a communication interface 401g, and an image output interface 401h. The CPU 401a, ROM 401b, RAM 401c, hard disk 401d, readout device 401e, input/output interface 401f, communication interface 401g, and the image output interface 401h are connected to each other via a bus 401i.

The CPU 401a is capable of executing computer programs stored in the ROM 401b and computer programs loaded into the RAM 401c. The computer 401 acts as the control apparatus 4 through execution, by the CPU 401a, of an application program 404a that is described below. The ROM 401b is structured as a mask ROM, PROM, EPROM, EEPROM or the like, and stores computer programs to be executed by the CPU 401a and stores data to be used by the computer programs.

The RAM 401c is structured as an SRAM, DRAM or the like. The RAM 401c is used for reading computer programs stored in the ROM 401b and the hard disk 401d. The RAM 401c is used as a work area for the CPU 401a when the CPU 401a executes these computer programs.

Installed in the hard disk 401d are: various computer programs to be executed by the CPU 401a, such as an operating system and application programs; and data to be used for executing these computer programs. The application program 404a used for performing a remaining reagent amount obtaining process according to the present embodiment is also installed in the hard disk 401d. Further, in the present embodiment, the hard disk 401d stores tables such as a reagent master, a reagent lot master, and a container master that are described later.

The readout device 401e is structured as a flexible disc drive, CD-ROM drive, DVD-ROM drive or the like. The readout device 401e is capable of reading a computer program or data, which is stored in a portable storage medium 404. The portable storage medium 404 stores therein the application program 404a according to the present embodiment. The computer 401 is capable of reading the application program 404a from the portable storage medium 404 to install the read application program 404a in the hard disk 401d.

Note that, the application program 404a can be provided to the computer 401 not only via the portable storage medium 404, but also from an external device via a telecommunication line (regardless of whether wired or wireless), which external device is communicably connected to the computer 401 by the telecommunication line. For example, the application program 404a is stored in a hard disk of a server computer on the Internet. The computer 401 can access the server computer, and download the application program 404a from the server computer and install the application program 404a in the hard disk 401d.

Also, an operating system that provides a graphical user interface environment, for example, Windows (registered trademark) manufactured and sold by Microsoft Corporation, is installed in the hard disk 401d. In the description below, it is assumed that the application program 404a according to the present embodiment runs on the operating system.

For example, the input/output interface 401f is configured as: a serial interface such as USB, IEEE1394 or RS-232C; a parallel interface such as SCSI, IDE or IEEE1284; or an analogue interface including a D/A converter, A/D converter and the like. The keyboard 4c is connected to the input/output interface 401f. A user can input data to the computer 401 by using the keyboard 4c.

The communication interface 401g is an Ethernet (registered trademark) interface, for example. The computer 401 is capable of transmitting/receiving data to/from the measurement mechanism section 2 via the communication interface 401g, using a predetermined communication protocol. The image output interface 401h is connected to the display section 4b that is structured with LCD, CRT or the like. Video signals corresponding to image data, which are supplied from the CPU 401a, are outputted to the display section 4b. The display section 4b displays an image (screen) in accordance with the inputted video signals.

Figure 3:
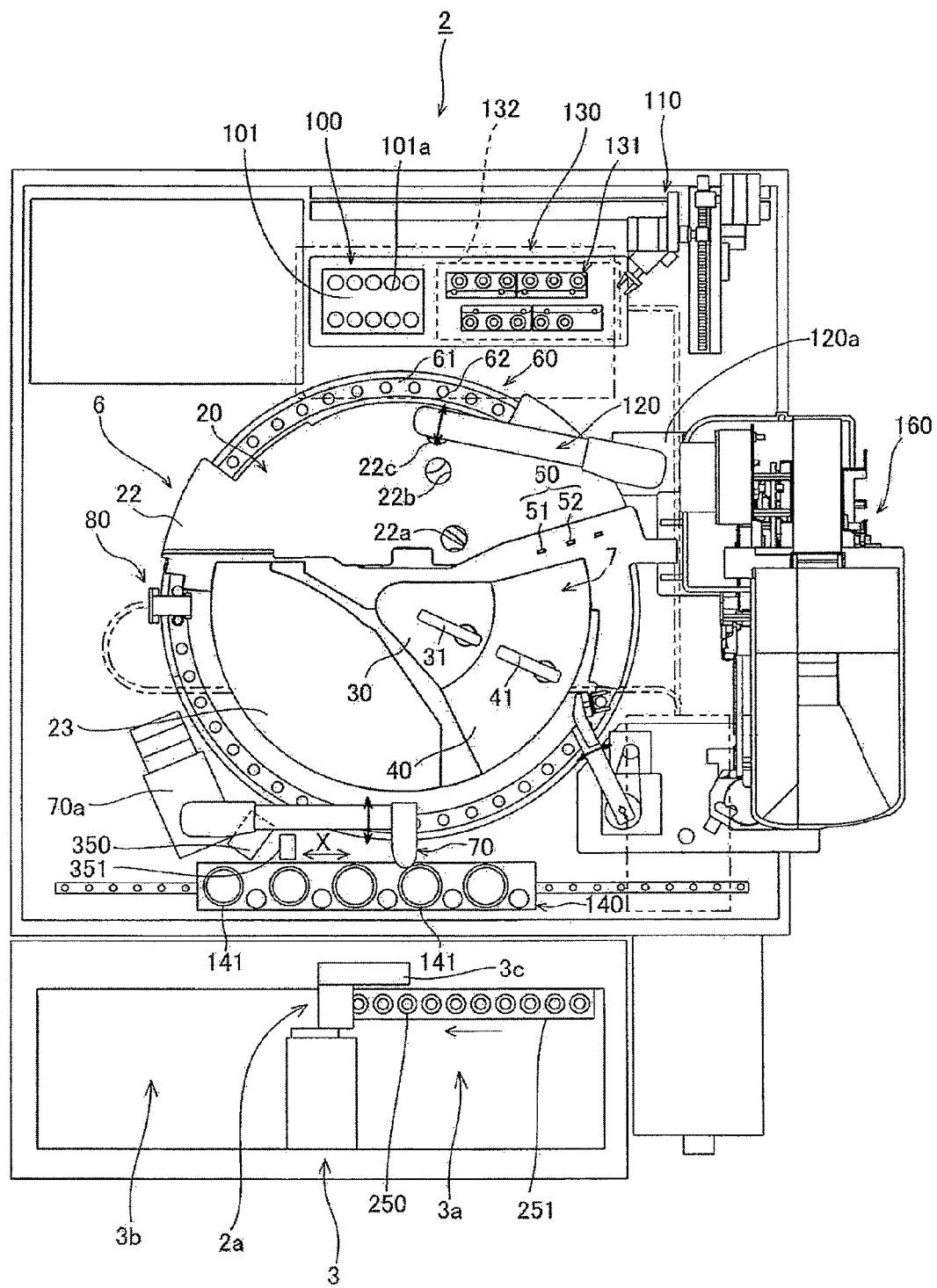
FIG. 3 is a plane view of a measurement mechanism section of the sample analyzer shown in FIG. 1.

As shown in FIGS. 1 to 3, in order to supply samples to the measurement mechanism section 2, the transport mechanism section 3 has a function to transport, to an aspirating position 2a (see FIG. 3) of the measurement mechanism section 2, a rack 251 that has mounted thereon a plurality of test tubes 250 (ten test tubes in the present embodiment), each of which contains a sample. The transport mechanism section 3 has a rack set region 3a for setting therein the rack 251 that accommodates test tubes 250 each containing an unprocessed sample, and has a rack storing region 3b for storing therein the rack 251 that accommodates test tubes 250 each containing a processed sample.

The measurement mechanism section 2 is configured to be able to optically measure a sample supplied from the transport mechanism section 3, thereby obtaining optical information about the supplied sample. In the present embodiment, the optical measurement is performed on a sample that has been dispensed from a test tube 250 mounted on the rack 251 of the transport mechanism section 3 into a cuvette 200 in the measurement mechanism section 2. Further, as shown in FIG. 3, the measurement mechanism section 2 includes a reagent storing section 6 for storing reagents, and a reagent replacement section 7 for performing replacement or addition of reagents.

Figure 11:
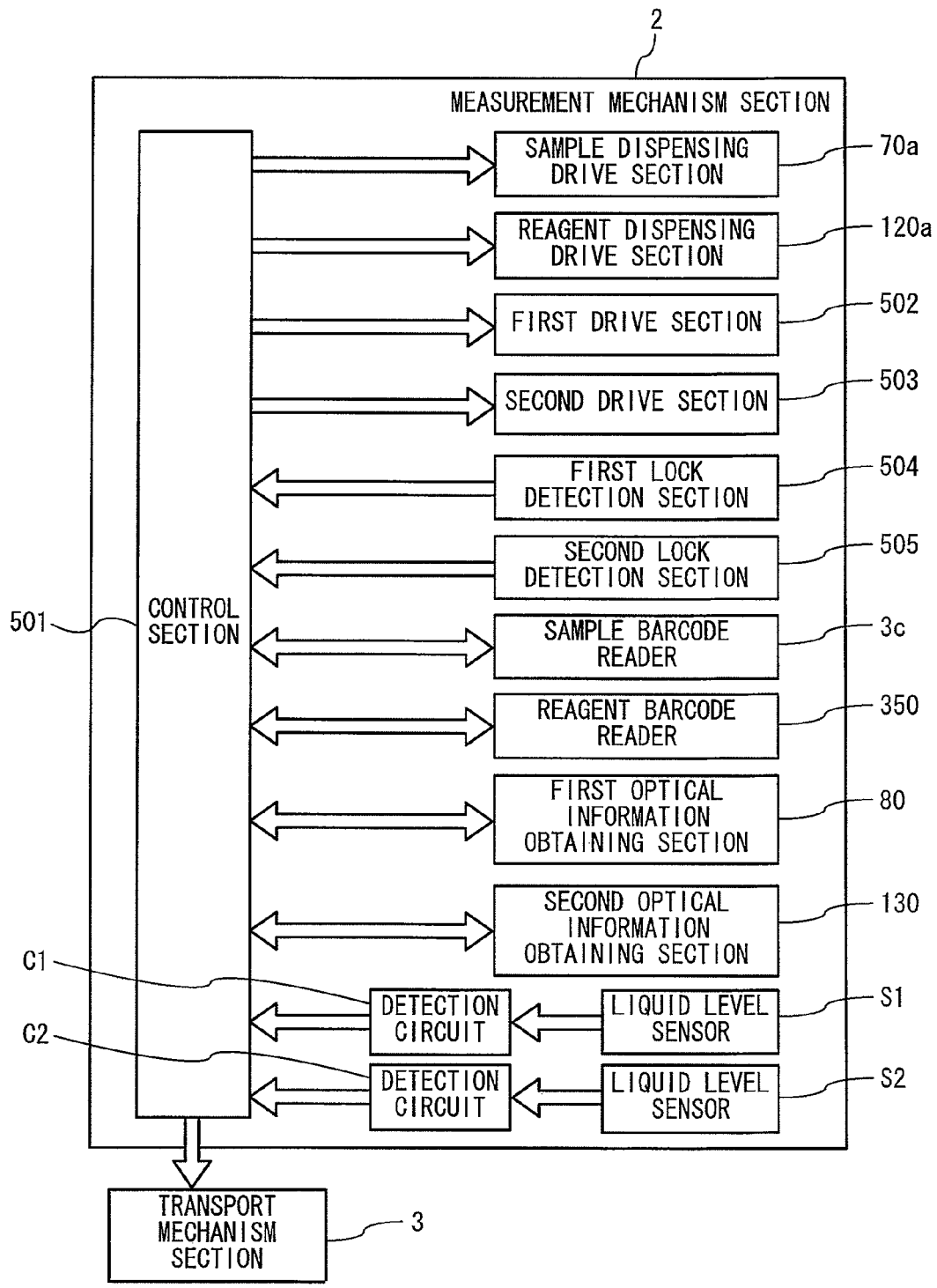
FIG. 11 is a block diagram showing the sample analyzer shown in FIG. 1.

As shown in FIG. 11, the measurement mechanism section 2 includes a sample dispensing drive section 70a, a reagent dispensing drive section 120a, a first drive section 502, a second drive section 503, a first lock detection section 504, a second lock detection section 505, a reagent bar code reader 350, a sample bar code reader 3c, a first optical information obtaining section 80, a second optical information obtaining section 130, a detection circuit C1, a detection circuit C2, and a control section 501 electrically connected to the transport mechanism section 3 or the like.

The sample dispensing drive section 70a includes: a stepping motor section 70b having a function to cause a sample dispensing arm 70 that is described later (see FIGS. 3 and 5) to rotate, ascend, or descend; a drive circuit (not shown) for driving the stepping motor section 70b; and a pump (not shown) for aspirating and dispensing a sample.

The reagent dispensing drive section 120a includes: a stepping motor section 120b having a function to cause a reagent dispensing arm 120 that is described later (see FIGS. 3 and 5) to rotate, ascend, or descend; a drive circuit (not shown) for driving the stepping motor section 120b; and a pump (not shown) for aspirating and dispensing a reagent.

The first drive section 502 includes: a first stepping motor (not shown) having a function to cause a first reagent table 11 (see FIG. 5) that is described later to rotate; and a drive circuit (not shown) for driving the first stepping motor. The first reagent table 11 rotates in accordance with the number of pulses of a drive pulse signal supplied from the control section 501 to the first drive section 502, and then stops.

Similarly, the second drive section 503 includes: a second stepping motor (not shown) having a function to cause a second reagent table 12 (see FIG. 5) that is described later to rotate; and a drive circuit (not shown) for driving the second stepping motor. The second reagent table 12 rotates in accordance with the number of pulses of a drive pulse signal supplied from the control section 501 to the second drive section 503, and then stops.

Note that, the control section 501 is capable of, by counting the number of pulses of the drive pulse signals which the control section 501 has supplied, determining the amounts of rotational movement of the first reagent table 11 and the second reagent table 12 from original positions of the first reagent table 11 and the second reagent table 12, respectively, thereby controlling the rotational movement of the first reagent table 11 and the second reagent table 12.

The first lock detection section 504 has a function to detect a lock state of a first cover 30 (see FIG. 3) that is described later, and transmit a lock signal to the control section 501 when the first cover 30 is locked. Similarly, the second lock detection section 505 has a function to detect a lock state of a second cover 40 (see FIG. 3) that is described later, and transmit a lock signal to the control section 501 when the second cover 40 is locked.

The reagent bar code reader 350 has a function to read bar codes on each of the first reagent table 11 and the second reagent table 12, and is provided near a sidewall 21 of the reagent storing section 6 that is described later, in such a manner as to have a predetermined distance from the reagent storing section 6 (see FIGS. 3 to 5). The reagent bar code reader 350 is capable of transmitting/receiving data to/from the control section 501, and has a drive circuit (not shown) for controlling ON/OFF of the reagent bar code reader 350. Note that, the reagent bar code reader 350 is always in a fixed position.

The sample bar code reader 3c has a function to read a bar code affixed to a test tube 250 containing a sample, which test tube 250 is mounted on the rack 251 having been transported by the transport mechanism section 3. The sample bar code reader 3c is provided near the aforementioned aspirating position 2a of the measurement mechanism section 2, so as to face the rack 251 transported by the transport mechanism section 3 (see FIGS. 3 to 5). The sample bar code reader 3c is capable of transmitting/receiving data to/from the control section 501, and has a drive circuit (not shown) for controlling ON/OFF of the sample bar code reader 3c. Note that, the sample bar code reader 3c is always in a fixed position.

The first optical information obtaining section 80 and the second optical information obtaining section 130 (see FIGS. 3 and 5) each have a function to obtain optical information about a sample, and are each configured to be able to transmit/receive data to/from the control section 501. The first optical information obtaining section 80 and the second optical information obtaining section 130 will be described later.

The detection circuit C1 is electrically connected to a liquid level sensor S1 provided at the tip of a pipette part 121 (reagent pipette) of the reagent dispensing arm 120 that is described later. The detection circuit C2 is electrically connected to a liquid level sensor S2 provided at the tip of a pipette part (sample pipette) of the sample dispensing arm 70 that is described later.

As shown in FIG. 12, main components of the control section 501 are a CPU 501a, a ROM 501b, a RAM 501c, and a communication interface 501d. The CPU 501a is capable of executing computer programs stored in the ROM 501b and computer programs loaded into the RAM 501c. The ROM 501b stores computer programs to be executed by the CPU 501a, and stores data to be used for the execution of the computer programs. The RAM 501c is used for reading the computer programs stored in the ROM 501b. The RAM 501c is also used as a work area of the CPU 501a at the time of execution of these computer programs.

The communication interface 501d is connected to the control apparatus 4. The communication interface 501d has a function to transmit optical information about a sample to the control apparatus 4, and receive a signal from the control section 4a of the control apparatus 4. Further, the communication interface 501d has a function to transmit commands, provided from the CPU 501a, for driving the respective components of the transport mechanism section 3 and the measurement mechanism section 2.

As shown in FIG. 3, the measurement mechanism section 2 includes the reagent storing section 6 for storing reagents and a reagent replacement section 7 for performing replacement or addition of reagents. The reagent storing section 6 is provided in order to refrigerate, at a low temperature (approximately 10° C.), reagent containers 300 containing the reagents to be added to the samples in the cuvettes 200, and to transport the reagent containers 300 in a rotation direction of the reagent storing section 6. Storing the reagents at such a low temperature suppresses alteration of the reagents. As shown in FIGS. 3 to 5, the reagent storing section 6 includes: a reagent transport section 10 (see FIGS. 4 and 5) for holding the reagents and transporting the reagents by rotating; and an outer wall portion 20 (see FIG. 3) that is provided so as to cover the sides and the top of the reagent transport section 10. The reagent transport section 10 holding the reagents is positioned at a refrigeration area that is formed with the outer wall portion 20, and the first and second covers 30 and 40 of the reagent replacement section 7 that is described later.

Figure 4:
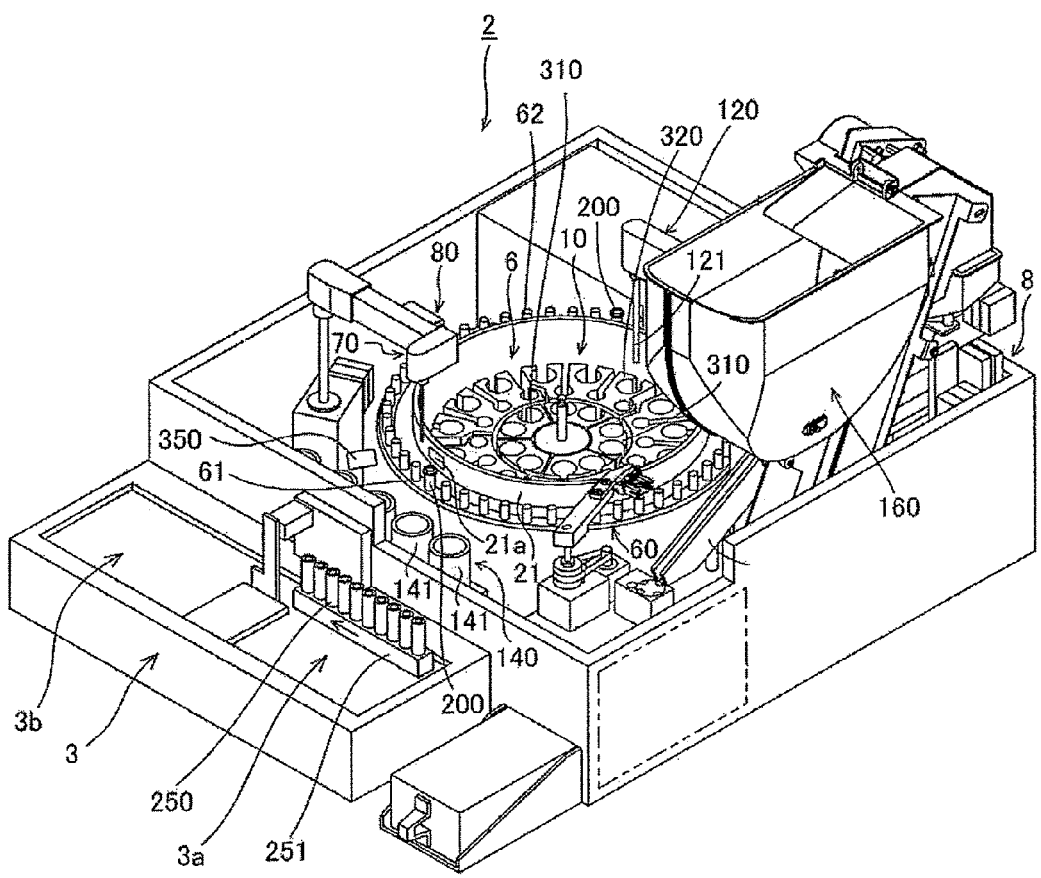
FIG. 4 is a perspective view showing the inside of the measurement mechanism section and a reagent storing section.
Figure 5:
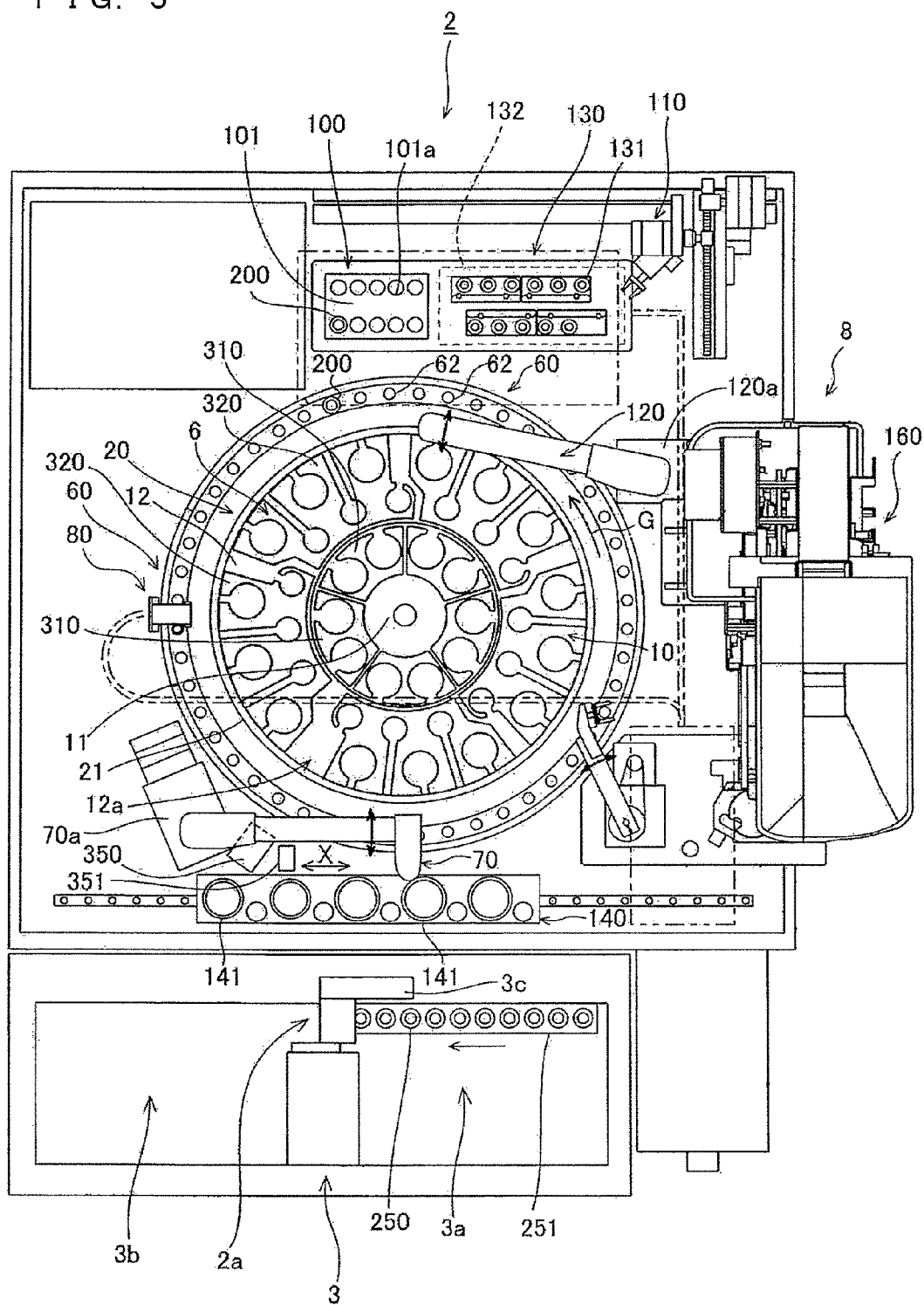
FIG. 5 is a plane view showing the inside of the measurement mechanism section and the reagent storing section shown in FIG. 4.

As shown in FIG. 5, the reagent transport section 10 includes: the round-shaped first reagent table 11 and the annular-shaped second reagent table 12 that is provided outside the first reagent table 11 so as to be concentric with respect to the first reagent table 11. The first reagent table 11 and the second reagent table 12 are configured such that first reagent container racks 310 and second reagent container racks 320, each of which holds reagent containers 300, are placed, in a removable manner, on the first reagent table 11 and the second reagent table 12, respectively. The outer wall portion 20 is formed with the sidewall 21 (see FIG. 4), a top surface 22 (see FIG. 3) fixed to the sidewall 21, and a cover 23 (see FIG. 3) that is removable. The reagent bar code reader 350 is provided near the sidewall 21 (see FIG. 4) of the reagent storing section 6 in such a manner as to have a predetermined distance from the reagent storing section 6.

The first reagent table 11 and the second reagent table 12 are each configured to be rotatable in both the clockwise direction and the counterclockwise direction. The first reagent table 11 and the second reagent table 12 are also configured to be rotatable independently from each other. Accordingly, the first reagent container racks 310 and the second reagent container racks 320, each of which holds reagent containers 300 each containing a reagent, are transported by the first reagent table 11 and the second reagent table 12, respectively, in rotation directions. Transporting the reagent containers 300 in such rotation directions allows, when the below-described reagent dispensing arm 120 performs reagent dispensing, a reagent that is to be dispensed, to be positioned near the reagent dispensing arm 120.

A heat insulating material (not shown) is attached to the sidewall 21 of the outer wall portion 20 so that cold air within the reagent storing section 6 (refrigeration area) will not escape therefrom. Further, as shown in FIG. 4, the sidewall 21 of the outer wall portion 20 has, at a position facing the reagent bar code reader 350, a shutter 21a that can be opened/shut. The shutter 21a is configured to be opened only when the reagent bar code reader 350 reads bar codes of the reagent containers 300, of the first reagent container racks 310, and of the second reagent container racks 320. This suppresses the cold air within the reagent storing section (refrigeration area) from escaping to the outside.

Further, as shown in FIG. 3, the top surface 22 of the outer wall portion 20 has three holes 22a, 22b and 22c. Through these three holes 22a, 22b and 22c, the reagent dispensing arm 120 aspirates the reagents stored in the reagent storing section 6.

When the cover 23 is removed together with the first cover 30 and the second cover 40 that are described later, a half-circle-shaped opening is formed at the reagent storing section 6 (refrigeration area). At the start of the measurement performed by the sample analyzer 1, the first reagent container racks 310 and the second reagent container racks 320 are placed in the reagent storing section 6 through the opening.

Figure 7:
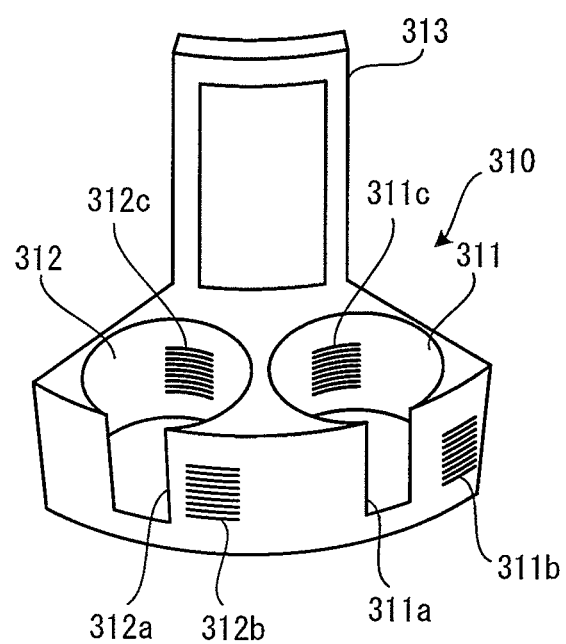
FIG. 7 is a perspective view showing an example of a first reagent container rack.
Figure 9:
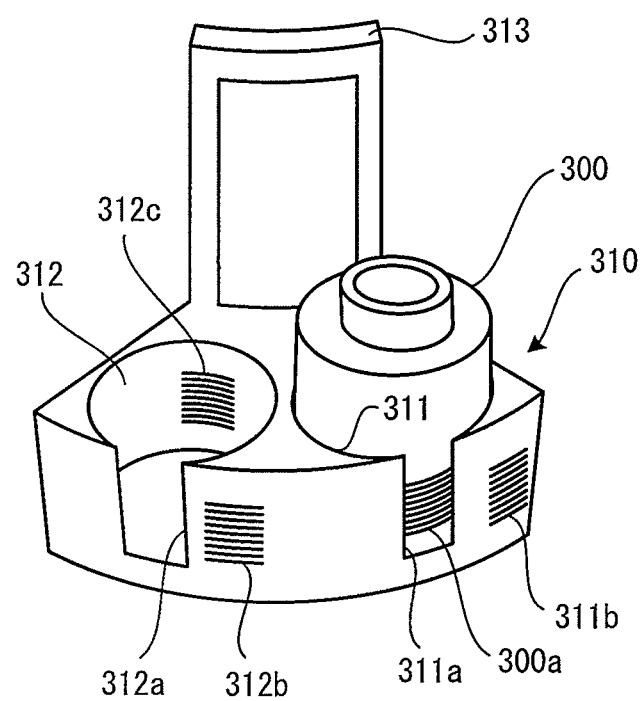
FIG. 9 is a perspective view showing that a reagent container is held by the first reagent container rack shown in FIG. 7.

As shown in FIG. 5, five first reagent container racks 310 can be placed on the first reagent table 11. Reagent containers 300 are placed, in an annular formation, in these five first reagent container racks 310. As shown in FIGS. 7 and 9, each first reagent container rack 310 includes: two holders 311 and 312 for holding reagent containers 300; and a notch 311a and a notch 312a that are provided at the front surface of the holder 311 and the front surface of the holder 312, respectively; and one grip portion 313 that is formed so as to protrude upwards. As shown in FIG. 7, the holders 311 and 312 are, when viewed in a plane view, each formed in a round shape. By inserting cylindrical reagent containers 300 into the holders 311 and 312, these reagent containers 300 can be held by the holders 311 and 312. By attaching an adaptor (not shown) to the holder 311 (or 312), the holder 311 (or 312) is able to hold a reagent container 300 having a smaller outer diameter than the inner diameter of the holder 311 (or 312). The first reagent container racks 310 include two types of racks that are formed such that each type of rack accommodates a different combination of inner diameter sizes of the holders 311 and 312. A user can change the rack type as appropriate so as to accommodate various sizes of reagent containers 300. Further, bar codes 311b and 312b are provided on front sides of outer side surfaces of the holders 311 and 312, respectively, and bar codes 311c and 312c are provided on inner side surfaces of the holders 311 and 312, respectively.

The two holders 311 and 312 are each capable of holding one of a plurality of reagent containers 300 that contain various reagents that are added to samples when measurement specimens are prepared from the samples. That is, ten reagent containers 300 at the maximum (2×5=10) can be placed on the first reagent table 11. The notches 311a and 312a are provided so as to allow the reagent bar code reader 350 (see FIG. 5) to read the bar codes 311c and 312c, respectively. The grip portion 313 is held when a first reagent container rack 310 is removed from the reagent storing section 6.

The bar codes 311b and 312b contain pieces of positional information (holder numbers) for identifying positions of the holders 311 and 312, respectively. The bar codes 311c and 312c contain pieces of information that indicate absence of reagent containers 300 held by the holders 311 and 312, respectively (hereinafter, referred to as reagent container absence information). A bar code 300a of each reagent container 300 contains information that specifies details of the reagent contained therein (information such as a reagent name, reagent container type, lot number, reagent expiration date, and the like).

Figure 8:
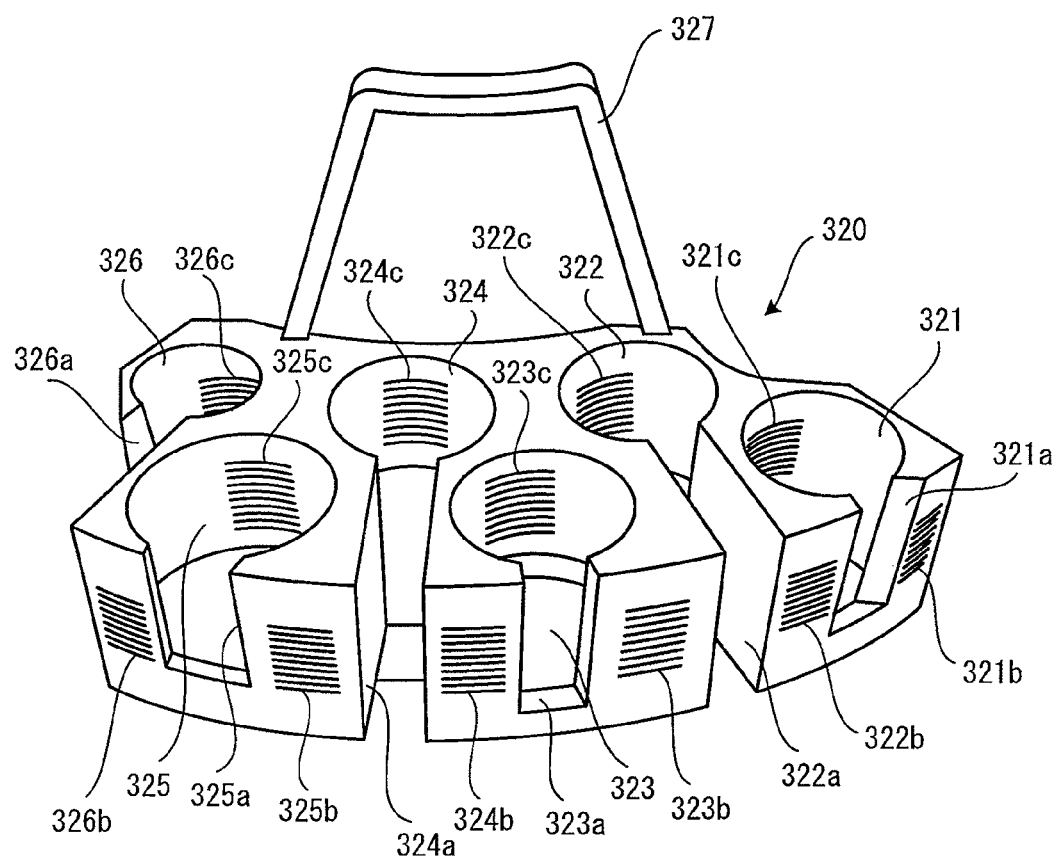
FIG. 8 is a perspective view showing an example of a second reagent container rack.
Figure 10:
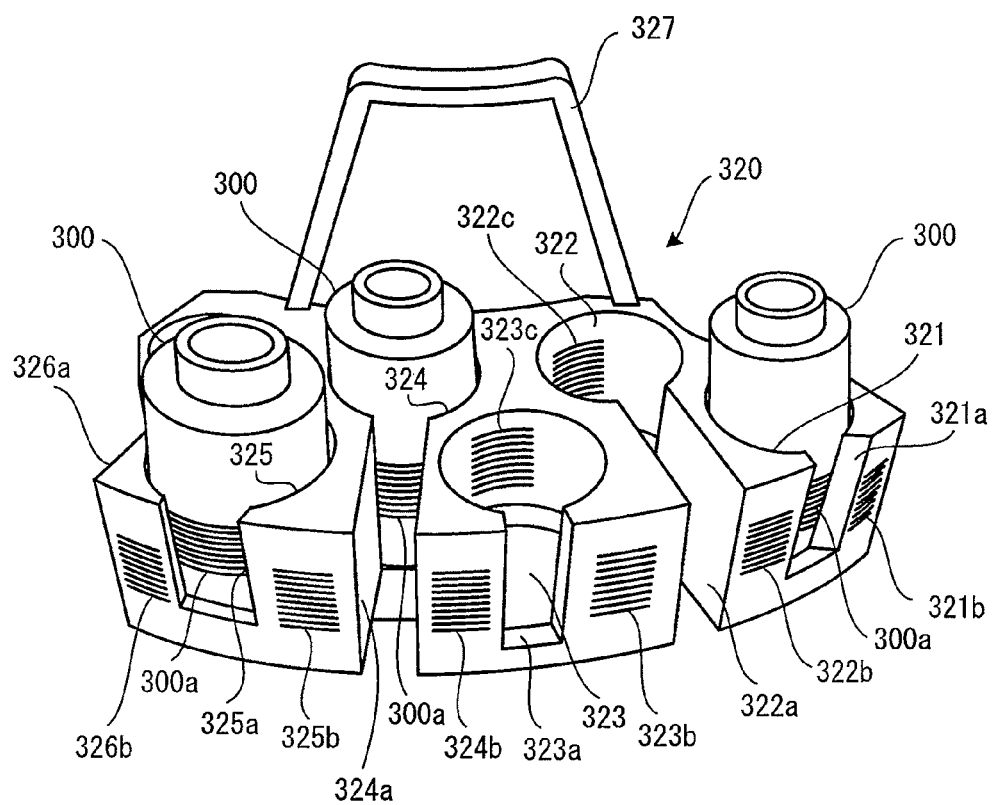
FIG. 10 is a perspective view showing that reagent containers are held by the second reagent container rack shown in FIG. 8.

As shown in FIG. 5, five second reagent container racks 320 can be placed on the second reagent table 12. Reagent containers 300 are placed, in an annular formation, on these five second reagent container racks 320. There are five gaps among these adjoining second reagent container racks 320. One of the gaps is greater than the other four gaps. Through a gap 12a that is this greater gap, the reagent bar code reader 350 positioned outside the reagent storing section 6 reads the bar codes 311b and 312b of the first reagent container racks 310 that are placed on the first reagent table 11 positioned inside the second reagent table 12, and reads the bar codes 300a of the reagent containers 300 held by the first reagent container racks 310. As shown in FIG. 8 and FIG. 10, the second reagent container racks 320 each include: six holders 321 to 326 for holding reagent containers 300; notches 321a to 326a that are provided at the front surfaces of the holders 321 to 326, respectively; and one grip portion 327 that is formed so as to protrude upwards. Similarly to the first reagent container racks 310, the holders 321 to 326 of each second reagent container rack 320 are, when viewed in a plane view, each formed in a round shape. By inserting cylindrical reagent containers 300 into the holders 321 and 326, these reagent containers 300 can be held by the holders 321 and 326. The second reagent container racks 320 include three types of racks such that each type of rack accommodates a different combination of inner diameter sizes of the holders 321 to 326. The second reagent container racks 320 are configured so that the same reagent containers as those placed on the first reagent container racks 310 can be placed on the second reagent container racks 320.

Barcodes 321b and 322b are provided to both sides of the notch 321a that is positioned at the front side of the holder 321. Similarly, bar codes 323b and 324b are provided to both sides of the notch 323a, and bar codes 325b and 326b are provided to both sides of the notch 325a. Further, bar codes 321c to 326c are provided on the inner surfaces of the holders 321 to 326, respectively.

The bar codes 321b to 326b contain pieces of positional information (holder numbers) for identifying positions of the holders 321 to 326, respectively. The bar codes 321c to 326c contain pieces of information that indicate absence of reagent containers 300 held by the holders 321 to 326 (reagent container absence information).

The control section 4a is configured to refer to, based on the bar code information read by the reagent bar code reader 350, tables such as the below-described reagent master, reagent lot master, container master, and the like that are stored in the hard disk 401d, thereby obtaining reagent identification information such as holder numbers, reagent names, lot numbers, reagent container types, reagent expiration dates, and the like. The obtained reagent identification information is configured to be stored in a reagent information database 36 (see FIG. 19) stored in the hard disk 401d. As shown in FIG. 19, the reagent information database 36 is a relational database that has fields for the holder numbers, reagent names, lot numbers, reagent container types, reagent expiration dates, and the like. The reagent information database 36 also has fields for remaining reagent amount information that contains usable amounts (remaining reagent amounts) and the numbers of remaining tests. The information stored in the reagent information database 36 is configured to be shown, by the control section 4a of the control apparatus 4, on the display section 4b.

As shown in FIGS. 1 and 2, the reagent replacement section 7 is provided near the central portion of the sample analyzer 1. Here, in the present embodiment, as shown in FIG. 3, the reagent replacement section 7 includes the first cover 30 and the second cover 40 which are both removable and which have a lock mechanism 31 and a lock mechanism 41, respectively, and includes a notification section 50 for notifying the user of a transportation state of the first reagent table 11 and a transportation state of the second reagent table 12.

The first cover 30 is configured to be removable when replacement of the reagent containers 300 placed on the first reagent table 11 (first reagent container rack 310) is performed. The lock mechanism 31 of the first cover 30 is provided for locking and fixing the first cover 30 during normal usage or after replacement or addition of reagents are completed, and for allowing the control section 4a to recognize the completion of the replacement or addition of reagents on the first reagent table 11.

The second cover 40 is configured so as to be removable when replacement of the reagent containers 300 placed on the second reagent table 12 (second reagent container rack 320) is performed. The lock mechanism 41 of the second cover 40 is provided for locking and fixing the second cover 40 during normal usage or after replacement or addition of reagents are completed, and for allowing the control section 4a to recognize the completion of the replacement or addition of reagents on the second reagent table 12.

The notification section 50 includes two LED indicators 51 and 52. As shown in FIG. 1 and FIG. 3, the two LED indicators 51 and 52 are arranged near the second cover 40, and are visually recognizable by the user from the outside of the sample analyzer 1. The LED indicators 51 and 52 are capable of illuminating in either blue or red.

The LED indicator 51 has a function to notify the user that a first reagent container rack 310 corresponding to a reagent, on the first reagent table 11, specified by the user has been moved to a removal position (below the first cover 30) where replacement of the reagent can be performed. To be specific, the LED indicator 51 is configured to illuminate in red when the first reagent table 11 is rotating and moving, and illuminate in blue when the first reagent container rack 310 corresponding to the specified reagent on the first reagent table 11 has been moved and then stopped at the removal position. This allows the user to be notified of a timing of removing the first cover 30 for replacement or addition of reagents.

The LED indicator 52 has a function to notify the user that a second reagent container rack 320 corresponding to a reagent, on the second reagent table 12, specified by the user has been moved to a removal position (below the second cover 40) where replacement of the reagent can be performed. Similarly to the LED indicator 51, the LED indicator 52 is configured to illuminate in red when the second reagent table 12 is rotating and moving, and illuminate in blue when the second reagent container rack 320 corresponding to the specified reagent on the second reagent table 12 has been moved and then stopped at the removal position.

The sample analyzer 1 is configured to automatically read, when the user locks the first cover 30 or the second cover 40 after replacement or addition of reagents has been completed, the bar codes 300a of all the reagent containers 300 held by the first reagent container rack 310, or the second reagent container rack 320, which holds the replacing or added reagents. In this manner, for example, even in the case where a reagent replacement instruction is provided specifying only one reagent, and reagents other than the specified reagent which are accommodated in the same first reagent container rack 310 or the second reagent container rack 320 are also replaced in addition to the specified reagent, the arrangement of reagents after the replacement can be properly recognized.

As shown in FIGS. 3 to 5, the measurement mechanism section 2 further includes a cuvette transporting section 60, the sample dispensing arm 70, the first optical information obtaining section 80, a lamp unit 90, a heating section 100, a cuvette transfer section 110, the reagent dispensing arm 120, the second optical information obtaining section 130, an urgent sample setting section 140, a fluid section 150, and the cuvette supply mechanism section 160.

The cuvette transporting section 60 has a function to transport cuvettes 200 to the respective components of the sample analyzer 1. The cuvette transporting section 60 includes: an annular-shaped cuvette transporting table 61 provided outside the annular-shaped second reagent table 12; and a plurality of cylindrical cuvette holders 62 that are circumferentially arranged on the cuvette transporting table 61 with predetermined intervals. The cuvette holders 62 are each provided for holding one cuvette 200. Into the cuvettes 200 (FIG. 5) held by the cuvette holders 62 of the cuvette transporting table 61, samples contained in the test tubes 250 of the transport mechanism section 3 and reagents stored in the reagent storing section 6 are dispensed, whereby measurement specimens are prepared.

The sample dispensing arm 70 has a function to aspirate a sample contained in a test tube 250 that has been transported by the transport mechanism section 3 to the aspirating position 2a, and dispense the aspirated sample into a cuvette 200 held in a cuvette holder 62 on the cuvette transporting table 61.

The first optical information obtaining section 80 is configured to obtain optical information from the sample in order to measure presence/absence and density of interference substances (chyle, hemoglobin and bilirubin) in the sample before a reagent is added thereto.

The first optical information obtaining section 80 obtains the optical information about the sample before the second optical information obtaining section 130 optically measures the sample. The first optical information obtaining section 80 obtains the optical information (information obtained from light transmitted through the sample) from the sample within the cuvette 200 held by the cuvette holder 62 of the cuvette transporting table 61.

The first optical information obtaining section 80 is electrically connected to the control section 4a of the control apparatus 4, and the data (optical information) obtained by the first optical information obtaining section 80 is transmitted to the control section 4a of the control apparatus 4.

The heating section 100 includes a plate 101 that can be heated. Ten cuvette holders 101a each having a concave shape are provided on the heating section 100. The cuvette holders 101a are each capable of holding one cuvette 200. The heating section 100 has a function to heat, to approximately 37° C., samples having been dispensed into cuvettes 200 by holding the cuvettes 200 in the cuvette holders 101a for a few minutes.

The cuvette transfer section 110 is provided in order to transfer cuvettes 200 among the cuvette transporting section 60, the heating section 100, and the second optical information obtaining section 130.

As shown in FIGS. 3 to 5, the reagent dispensing arm 120 is provided for dispensing a reagent in a reagent container 300 mounted on the reagent storing section 6 into a cuvette 200, thereby mixing the reagent with a sample within the cuvette 200. Note that, the pipette part 121 of the reagent dispensing arm 120 has a heating function, and a reagent aspirated by the pipette part 121 is heated to approximately 37° C. instantaneously. That is, the reagent previously stored in the reagent storing section 6 at a low temperature (approximately 10° C.) is heated to approximately 37° C. by the reagent dispensing arm 120, and then mixed with the sample having been heated to approximately 37° C. In this manner, the reagent is added to the sample on which the optical measurement has been performed by the first optical information obtaining section 80, whereby the measurement specimen is prepared.

In the present embodiment, the reagent dispensing arm 120 is configured to move, through pulse control by a stepping motor (not shown), the pipette part 121 in the up/down directions when performing a dispensing operation. Also, the tip of the pipette part 121 of the reagent dispensing arm 120 is provided with the liquid level sensor S1 (see FIG. 11) for detecting the liquid level of a reagent when aspirating the reagent from a reagent container 300. Electrical information (change in electrostatic capacitance) that is generated when the liquid level sensor S1 contacts the surface of the reagent, is inputted to the detection circuit C1, and the detection circuit C1 performs predetermined processing on the inputted electrical information, whereby the liquid level of the reagent is detected. Accordingly, the height of the liquid level of the reagent in the reagent container 300 can be calculated based on the number of pulses supplied during a period until the surface of the reagent is detected and based on an amount by which the liquid level sensor S1 moves in response to one pulse. Steps of calculating the height of the liquid level of the reagent will be described later in detail.

In the present embodiment, in the case where an instruction to replace a reagent is provided during the operation of the reagent dispensing arm 120, if the dispensing operation is being performed on reagents to be dispensed which are placed on a reagent table that accommodates the reagent having been specified for the replacement, the dispensing operation, which is being performed by the reagent dispensing arm 120 on the reagents to be dispensed which are placed on the reagent table that accommodates the reagent having been specified for the replacement, is terminated. In this case, if the reagents to be dispensed are accommodated also on a different reagent table from the reagent table that accommodates the reagent having been specified for the replacement, the reagent dispensing arm 120 terminates the dispensing operation performed on the reagents to be dispensed which are placed on the reagent table that accommodates the reagent having been specified for the replacement, but continues the dispensing operation on the reagents to be dispensed which are accommodated on this different reagent table. Further, the reagent dispensing arm 120 is configured not to perform, when the replacement instruction is provided in the case where the reagents to be dispensed are placed only on the reagent table that accommodates the reagent having been specified for the replacement, the dispensing operation after completing dispensing the reagents to be dispensed, into samples being heated in the heating section 100 (samples waiting for the reagents to be dispensed thereinto). As a result, the samples that are being heated in the heating section 100 when the replacement instruction is provided, are also measured when a predetermined period has passed after the heating.

The second optical information obtaining section 130 has a function to measure optical information about a measurement specimen. As shown in FIG. 5, the second optical information obtaining section 130 includes a measurement-use mounting section 131 and a detection section 132 positioned below the measurement-use mounting section 131.

The detection section 132 of the second optical information obtaining section 130 is configured to be able to optically measure, under a plurality of conditions, a measurement specimen within a cuvette 200. The second optical information obtaining section 130 is electrically connected to the control section 4a of the control apparatus 4, and data obtained from the measurement (optical information) is transmitted to the control section 4a of the control apparatus 4. As a result, in the control apparatus 4, the data transmitted from the second optical information obtaining section 130 (optical information) is analyzed based on a result of analyzing the data (optical information) previously obtained from the first optical information obtaining section 80. Then, a result of the analysis is displayed on the display section 4b.

As shown in FIGS. 3 to 5, the urgent sample setting section 140 is provided for performing a sample analysis process on a sample that needs urgent analysis. The urgent sample setting section 140 is configured to be able to allow an urgent sample to cut in when a sample analysis process is being performed on samples supplied from the transport mechanism section 3. Further, the urgent sample setting section 140 is slidable in the X-direction, and is provided with five holders 141 for holding containers containing diluents and cleaning solutions (not shown). A bar code (not shown) is affixed to each of the containers containing the diluents and cleaning solutions (not shown). The bar codes of the diluents and cleaning solutions are configured to be read by the reagent bar code reader 351 when the urgent sample setting section 140 is being slid in the X-direction. Accordingly, the types, arrangement, and the like of the diluents and cleaning solutions are displayed on the display section 4b. Further, as shown in FIGS. 1 and 2, a cover 1c is provided in front of the reagent replacement section 7 of the sample analyzer 1. This cover 1c is removed when replacement or addition of the containers containing the diluents and cleaning solutions (not shown) is performed.

The cuvette supply mechanism section 160 is configured to be able to sequentially supply the cuvette transporting section 60 with a plurality of cuvettes 200 that have been fed by the user at random.

[Analysis Operation]

Next, a sample analysis operation performed by the sample analyzer 1 will be described in detail. First, initial setting (initializing process) of the sample analyzer 1 is performed when the measurement mechanism section 2 and the control apparatus 4 of the sample analyzer 1 shown in FIG. 4 are turned on.

Figure 13:
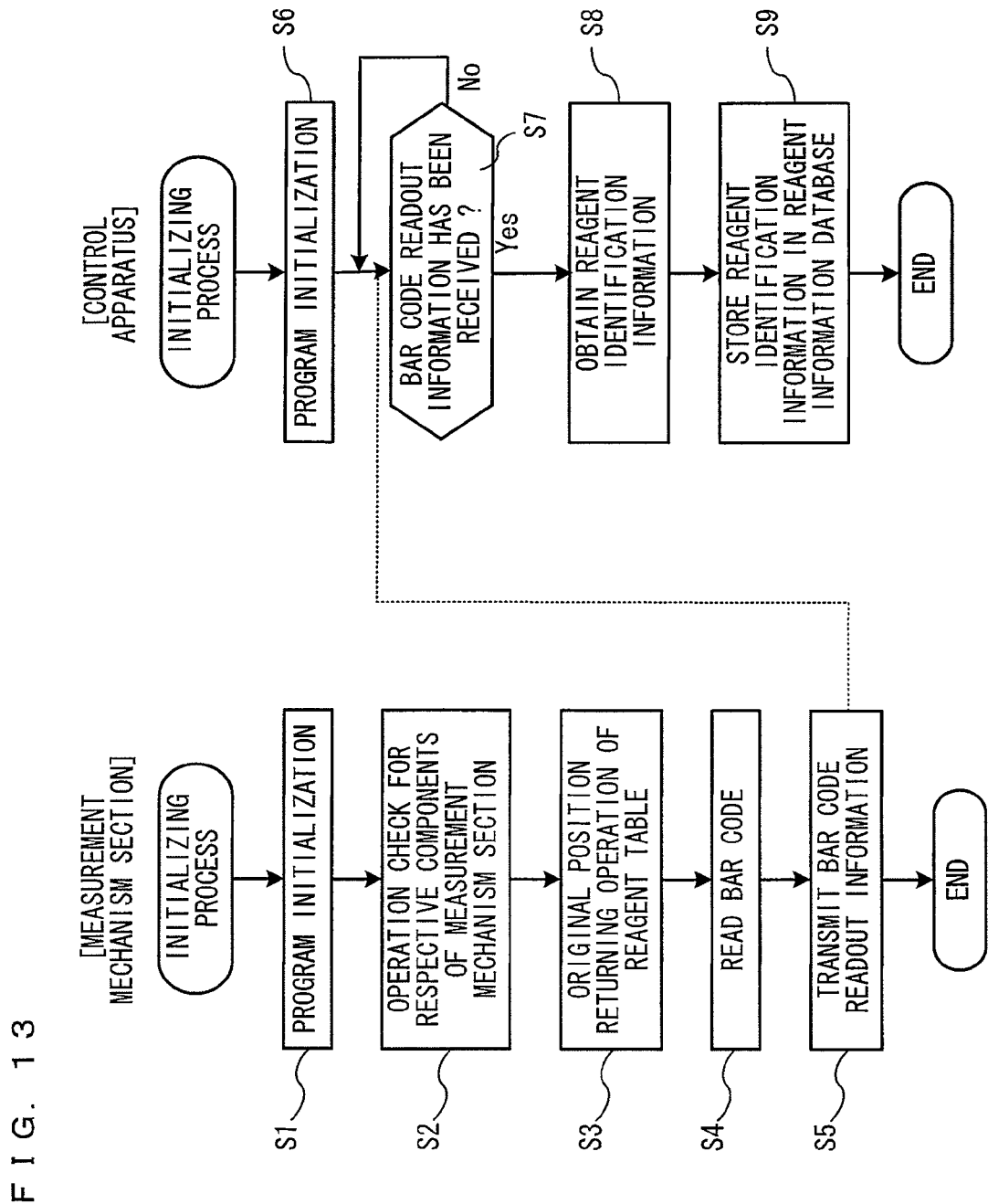
FIG. 13 is a flowchart showing an initializing process of the embodiment.

FIG. 13 is a flowchart showing the initializing process of the sample analyzer 1. As a result of turning on power to the measurement mechanism section 2 and the control apparatus 4, programs stored in the control section 501 of the measurement mechanism section 2 are initialized at step S1. Subsequently, at step S2, operation checks of the respective components included in the measurement mechanism section 2 such as the sample dispensing drive section 70a and the reagent dispensing drive section 120a (see FIG. 11) are performed. To be specific, operations for returning the respective mechanisms to their initial positions are performed, for example.

Then, at step S3, original position returning operation is performed in order to return the first reagent table 11 and the second reagent table 12 to their initial positions. Subsequently, at step S4, the reagent bar code reader 350 reads the bar codes of the first reagent container racks 310 placed on the first reagent table 11, the bar codes of the reagent containers 300 held by the first reagent container racks 310, the bar codes of the second reagent container racks 320 placed on the second reagent table 12, and the bar codes of the reagent containers 300 held by the second reagent container racks 320.

Next, at step S5, the read bar code information (bar code readout information) obtained at step S4 is transmitted to the control apparatus 4.

Meanwhile, also in the control apparatus 4, programs stored in the control section 4a of the control apparatus 4 are initialized at step S6 when the control apparatus 4 is turned on. Then, at step S7, the control section 4a of the control apparatus 4 determines whether or not the bar code readout information has been received. When the control section 4a determines that the bar code readout information has been received (determination "Yes"), the processing proceeds to step S8. At step S8, based on the bar code readout information (such as holder numbers, reagent IDs, container IDs, and the like), reagent identification information such as holder numbers, reagent names, lot numbers, reagent container types and the like, that is, information indicating what reagents are placed in which positions on the reagent tables, is obtained.

Then, at step S9, the "reagent identification information" obtained at step S8 is stored in the reagent information database 36 of the hard disk 401d. Note that, prior to storing the reagent identification information obtained at step S8, reagent identification information obtained from a previously performed bar code reading operation (holder numbers, reagent names, lot numbers, reagent container types, expiration dates, and the like) and remaining reagent amount information (usable amounts and the numbers of remaining tests) are already saved in the reagent information database 36. When storing, in the reagent information database 36, the reagent identification information obtained at step S8, the control section 4a determines whether or not the reagent identification information obtained at step S8 is the same as the reagent identification information saved in the reagent information database 36. If the newly obtained reagent identification information about a reagent is the same as the previously saved reagent identification information, a process of leaving the remaining reagent amount information about the reagent as it is in the reagent information database 36, is performed. If the newly obtained reagent identification information about a reagent is not the same as the previously saved reagent identification information, a process of deleting the remaining reagent amount information about the reagent from the reagent information database 36, is performed (a process of storing a "-(hyphen)" in the fields of "usable amount" and "number of remaining tests" in the reagent information database 36). By performing these processes, if, for example, reagent arrangement on the reagent tables is not changed at all between before turning off the sample analyzer and after turning on the sample analyzer, the remaining amount information about reagents on these tables can be left as it is in the reagent information database 36.

After the sample analyzer 1 has performed the initializing process, a menu screen (not shown) is displayed on the display section 4b. Then, as a result of the user pressing a start button displayed in the menu screen, a measurement start signal that provides an instruction to start the measurement is transmitted from the control apparatus 4 to the measurement mechanism section 2. A measurement start signal transmission process performed by the control apparatus 4 will be described later.

When the control section 501 of the measurement mechanism section 2 has received the measurement start signal, samples in a predetermined amount are dispensed by the sample dispensing arm 70 from the test tubes 250 mounted on the rack 251 into the cuvettes 200 on the cuvette transporting table 61. Next, the first optical information obtaining section 80 optically measures the samples, thereby obtaining optical information (first optical information) from the samples. The first optical information is transmitted to the control section 4a of the control apparatus 4.

Then, the control section 4a of the control apparatus 4 uses the received data (first optical information) to calculate absorbance of the samples as well as presence/absence and density of interference substances (chyle, hemoglobin and bilirubin) in the samples.

Subsequently, the control section 4a drives the reagent dispensing arm 120 and the sample dispensing arm 70 to add, to the samples in the cuvettes 200, reagents in the reagent containers 300 mounted on a reagent table (first reagent table 11 or second reagent table 12) and diluents in the containers held by the holders 141 of the urgent sample setting section 140. Note that, the measurement mechanism section 2 is configured such that, at the time of aspirating the reagents contained in the reagent containers, the reagent dispensing arm 120 and the sample dispensing arm 70 perform a liquid level detection process on the reagents to be aspirated, and liquid level detection information obtained as a result is transmitted to the control section 4a of the control apparatus 4. Then, the control section 4a calculates, based on the received liquid level detection information, a remaining amount of each reagent to be aspirated, and stores the remaining reagent amount information in the above-described reagent information database 36. The liquid level detection process performed by the measurement mechanism section 2 and the remaining reagent amount obtaining process performed by the control section 4a will be described later.

Thereafter, the detection section 132 of the second optical information obtaining section 130 optically measures the measurement specimens in the cuvettes 200 under a plurality of conditions, thereby obtaining optical information from the measurement specimens (second optical information).

Next, the second optical information obtained by the second optical information obtaining section 130 is transmitted to the control section 4a of the control apparatus 4. Based on the application program 404a installed in the hard disk 401d, the control section 4a having received the second optical information analyzes the second optical information and outputs analysis results.

Then, after the analysis by the control section 4a of the control apparatus 4 has ended, the obtained analysis results are displayed on the display section 4b of the control apparatus 4. This is the end of the sample analysis operation by the sample analyzer 1.

[Reagent Management Screen]

Figure 18:
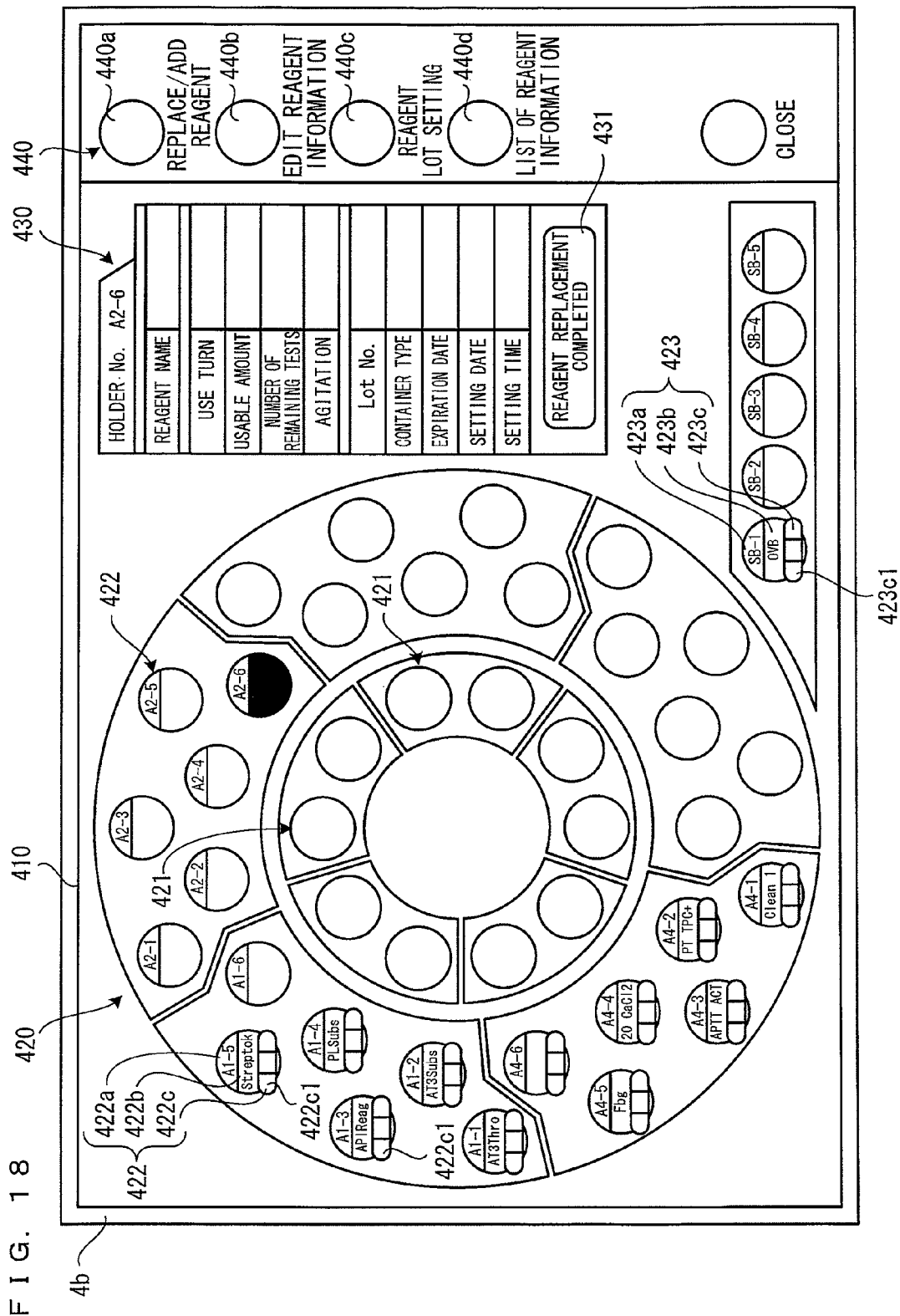
FIG. 18 shows an example of a reagent management screen displayed on a display section of the control apparatus.

In the present embodiment, as shown in FIG. 18, the display section 4b of the control apparatus 4 is capable of displaying a reagent management screen 410 that shows arrangement of the reagents in the reagent storing section 6. The reagent management screen 410 is displayed when a reagent button (not shown) displayed in the aforementioned menu screen is pressed. FIG. 18 shows an example of the reagent management screen displayed on the display section 4b. The reagent management screen 410 includes a reagent arrangement display area 420, a reagent detailed information display area 430, and an operation means display area 440. Note that, the display section 4b has touch panel functions. Accordingly, the user can select or operate buttons and the like displayed on the reagent management screen 410, by directly touching them.

Displayed in the reagent arrangement display area 420 are: ten (at maximum) first reagent indicia 421 that are displayed corresponding to an arrangement state of the reagents placed on the above-described first reagent table 11 that is positioned inside the second reagent table 12; thirty (at maximum) second reagent indicia 422 that are displayed corresponding to an arrangement state of the reagents placed on the above-described second reagent table 12 that is positioned outside the first reagent table 11; and five (at maximum) diluent/cleaning solution indicia 423 that are displayed corresponding to an arrangement state of diluents and cleaning solutions. These indicia are each displayed in a specifiable manner. Each second reagent indicium 422 includes: a position indicating portion 422a for indicating the position of a corresponding reagent; a reagent name indicating portion 422b for indicating the name of the corresponding reagent; and a remaining amount indicator 422c for indicating a remaining amount of the corresponding reagent. Although not shown for the sake of simplicity of the drawing, each first reagent indicium 421 similarly includes: a position indicating portion for indicating the position of a corresponding reagent; a reagent name indicating portion for indicating the name of the corresponding reagent; and a remaining amount indicator for indicating a remaining amount of the corresponding reagent. Note that, the remaining amount indicator 422c includes three small areas 422c1. The remaining reagent amount is indicated through coloring and uncoloring of these areas 422c1. To be specific, when the three areas 422c1 are all colored, this indicates a sufficient remaining reagent amount. The three areas 422c1 are sequentially uncolored in accordance with a decrease in the remaining reagent amount. Each diluent/cleaning solution indicium 423 includes: a position indicating portion 423a for indicating the position of a corresponding diluent or cleaning solution; a liquid name indicating portion 423b for displaying the name of the corresponding diluent or cleaning solution; and a remaining amount indicator 423c for indicating a remaining amount of the corresponding diluent or cleaning solution. Similarly to the remaining reagent amount indicator 422c, the remaining amount indicator 423c for each diluent/cleaning solution also includes three small areas 423c1, and is configured such that the remaining amount is indicated in the same manner as that of the remaining amount indicator 422c for each reagent.

Pieces of positional information (holder numbers) about the reagents, which are indicated in the position indicating portions 422a of the second reagent indicia 422, are indicated as a result of the reagent bar code reader 350 having read the bar codes 321b to 326b of the second reagent container racks 320 (see FIG. 10). Each reagent name indicated on the reagent name indicating portions 422b is indicated based on values, read by the reagent bar code reader 350 (see FIG. 5), of the bar code 300a of the corresponding reagent container 300 containing a reagent, with reference to the reagent master (table) stored in the hard disk 401d of the control section 4a, the reagent master showing a correspondence relationship between bar codes and reagent names. The position indicating portion 423a of each diluent/cleaning solution indicium is always displayed since the holders 141 (see FIG. 5), of the urgent sample setting section 140, for holding diluent/cleaning solution containers (not shown) each containing a diluent or a cleaning solution are fixed to the sample analyzer 1. Each diluent/cleaning solution name indicated on the liquid name indicating portions 423b is indicated based on values, read by the reagent bar code reader 351, of the bar code (not shown) of the corresponding diluent/cleaning solution container (not shown) containing a diluent or cleaning solution, with reference to the reagent master (table) stored in the hard disk 401d of the control section 4a, the reagent master showing a correspondence relationship between bar codes and names of diluents/cleaning solutions.

The reagent detailed information display area 430 displays detailed information about a reagent corresponding to a specified first reagent indicium 421 or second reagent indicium 422 (holder number, reagent name, use turn, usable remaining amount (usable amount), number of remaining tests, necessity/unnecessity of agitation, lot number, reagent container type, reagent expiration date, setting date, setting time, and the like). To be more specific, indicated in a field of "holder number" is positional information about the reagent, which is indicated in the position indicating portion of the specified reagent indicium. A field of "reagent name" indicates, in a similar manner to the reagent name indicating portion of the specified reagent indicium, a reagent name which is specified with reference to the reagent master and based on the values, read by the bar code reader 350, of the bar code 300a of the corresponding reagent container 300. Indicated in a field of "use turn" is the corresponding reagent's turn to be used in the measurement in the case where a plurality of identical reagents are placed on the reagent tables. Indicated in a field of "usable amount" is a remaining amount of the corresponding reagent to the specified reagent indicium. Indicated in a field of "number of remaining tests" is a value obtained from dividing the "usable amount" by the amount of reagent to be used in the measurement for once. A field of "agitation" indicates whether or not agitation of the corresponding reagent to the specified reagent indicium is necessary. Indicated in a field of "lot number" is a lot number that is specified with reference to the reagent lot master and based on the values, read by the reagent bar code reader 350, of the bar code 300a of the corresponding reagent container 300. Indicated in a field of "container type" is a container type that is specified with reference to the container master and based on the values, read by the reagent bar code reader 350, of the bar code 300a of the corresponding reagent container 300. Indicated in a field of "expiration date" is an expiration date corresponding to the lot number that is specified with reference to the reagent lot master and based on the values, read by the reagent bar code reader 350, of the bar code 300a of the corresponding reagent container 300. Indicated in fields of "setting date" and "setting time" are a date and time when the corresponding reagent to the specified reagent indicium has been set in the sample analyzer 1. Through this reagent detailed information, the user is able to manage the reagents, for example, determine a timing of replacement for each reagent.

The reagent detailed information display area 430 is further provided with a "REAGENT REPLACEMENT COMPLETED" button 431. The "REAGENT REPLACEMENT COMPLETED" button 431 has a function to manually cause the sample analyzer 1 to recognize replacement of the corresponding reagent when the sample analyzer 1 has not recognized the replacing reagent at the time of the reagent replacement. By pressing the "REAGENT REPLACEMENT COMPLETED" button 431 after specifying the replacing reagent, the bar code of the replacing reagent is automatically read by the bar code reader 350. Accordingly, the "setting date" and "setting time" in the reagent detailed information display area 430 are updated to the date and time at which the "REAGENT REPLACEMENT COMPLETED" button 431 has been pressed.

Figure 20:
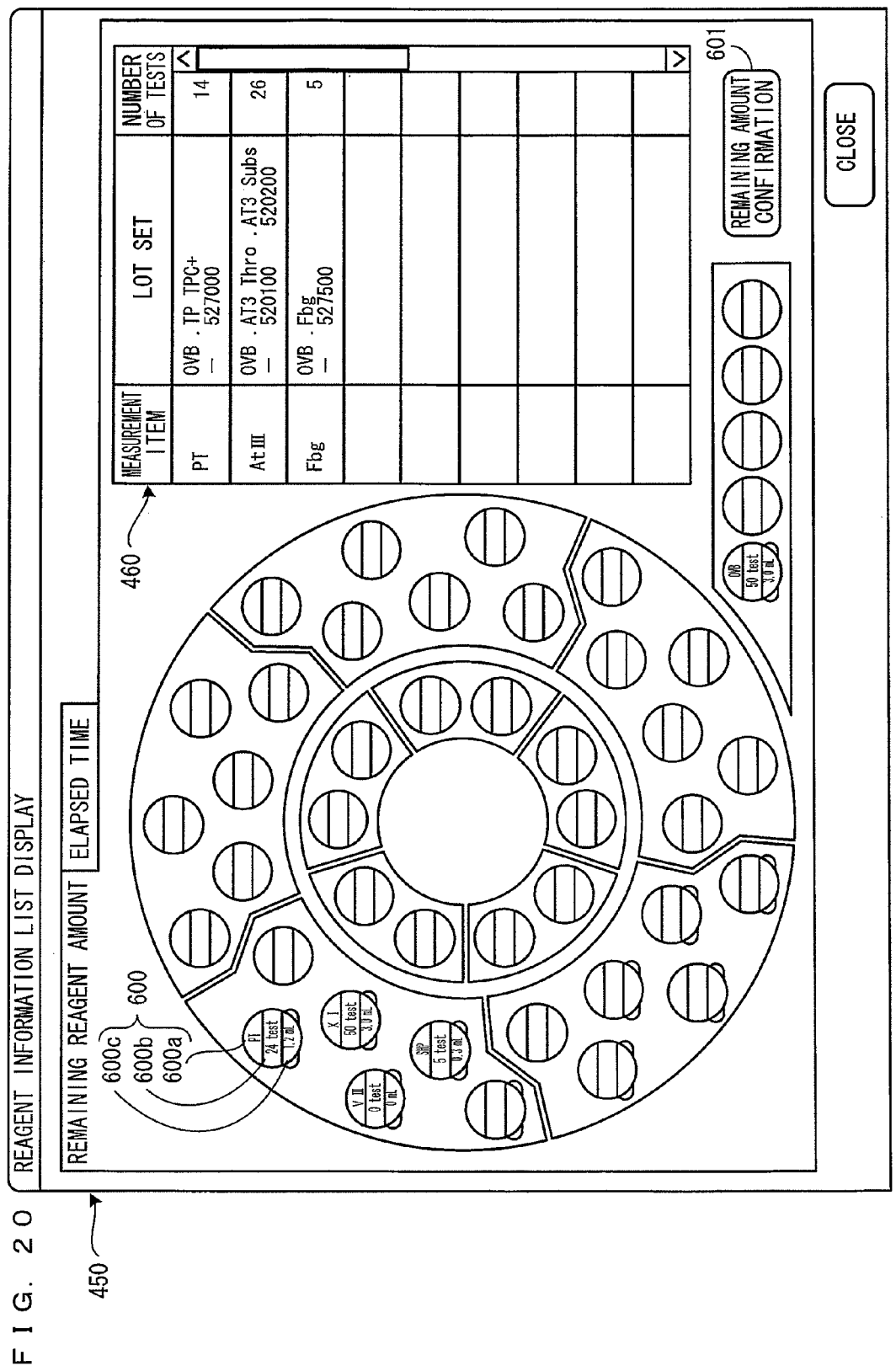
FIG. 20 shows an example of a reagent information list display screen.

The operation means display area 440 includes: a replacement/addition instruction button 440a for providing an instruction to replace or add a reagent; an edit button 440b for editing reagent information; a reagent lot setting button 440c for assigning a reagent lot to a measurement item; and a reagent information list button 440d. FIG. 20 shows an example of a reagent information list display screen. If, when the user wishes to know all the remaining reagent amounts, the user presses the reagent information list button 440d in the reagent management screen shown in FIG. 18, the display switches to a reagent information list display screen 450 as shown in FIG. 20.

A reagent indicium 600 includes a reagent name indicating portion 600a for displaying a reagent name, a test number indicating portion 600b for indicating the number of tests performable, and a remaining amount indicating portion 600c for displaying a remaining reagent amount. The test number and the remaining reagent amount are displayed only when the remaining reagent amount is known. Note that, in FIG. 20, a reagent indicium 600 of which these three indicating portions are blank indicates that a reagent rack is not set or a reagent container is not placed. In the case where the remaining reagent amount is unknown, only a reagent name such as "PT" is indicated in the reagent name indicating portion 600a that is a top portion of the reagent indicium 600, and the other middle and bottom portions are left blank. When the remaining amount is determined, "PT", "24 tests" and "1.2 ml" are indicated in the top, middle and bottom portions, respectively, for example. Note that, by properly selecting a background color of the reagent indicium 600, various information can be provided to the user. For example, when the remaining reagent amount is less than a predetermined amount ("warning" remaining amount) the reagent indicium 600 can be displayed in yellow. Further, when the remaining reagent amount does not even allow the measurement to be performed once and has a risk of causing interruption of the measurement during a measurement operation ("interruption" remaining amount), the reagent indicium 600 can be displayed in red. Displaying in this manner allows the user to prepare replacement of the corresponding reagent in advance.

In the example shown in FIG. 20, the number of measurement tests performable for each measurement item is indicated in an area 460 on the right side of the screen. To be specific, the number of measurement tests performable for each measurement item is calculated and indicated based on the information stored in the reagent information database 36 of the hard disk 401d, such as the remaining reagent amounts, a necessary type of reagent for each measurement item, and a necessary amount of reagent for each measurement item. In this case, if a plurality of lot sets exist for the same measurement item (if the same reagents having different lot numbers from each other are set in the sample analyzer), the number of performable measurement tests is displayed for each lot set in a different row in the column of "lot set". Further, when even one reagent, of which the remaining amount is unknown, exists among necessary reagents for a particular measurement item, the number of tests performable for this particular measurement item is not indicated.

A "REMAINING AMOUNT CONFIRMATION" button 601 is provided on the lower right side of the reagent information list display screen 450. The control section 4a of the control apparatus 4 is configured to start, when the "REMAINING AMOUNT CONFIRMATION" button 601 is pressed, the remaining reagent amount obtaining process for reagents whose remaining amounts are unknown from among the reagents placed in the reagent storing section 6. Note that, the control section 4a is configured to be able to accept an instruction to start the remaining reagent amount obtaining process, which is provided through the "REMAINING AMOUNT CONFIRMATION" button 601, during a period from when the above-described initializing process of the control apparatus 4 has ended until when a measurement start signal providing an instruction to start the measurement is transmitted to the measurement mechanism section 2, and also during a period from when the measurement operation of the measurement mechanism section 2 has ended until when a measurement start signal providing an instruction to start the next measurement is transmitted to the measurement mechanism section 2. The control section 4a is also configured not to accept an instruction to start the remaining reagent amount obtaining process, which is provided through the "REMAINING AMOUNT CONFIRMATION" button 601, during a period from when the measurement start signal has been transmitted to the measurement mechanism section 2 until when the measurement operation of the measurement mechanism section 2 ends. Hereinafter, the remaining reagent amount obtaining process will be described.

<Remaining Reagent Amount Obtaining Process>

Figure 14:
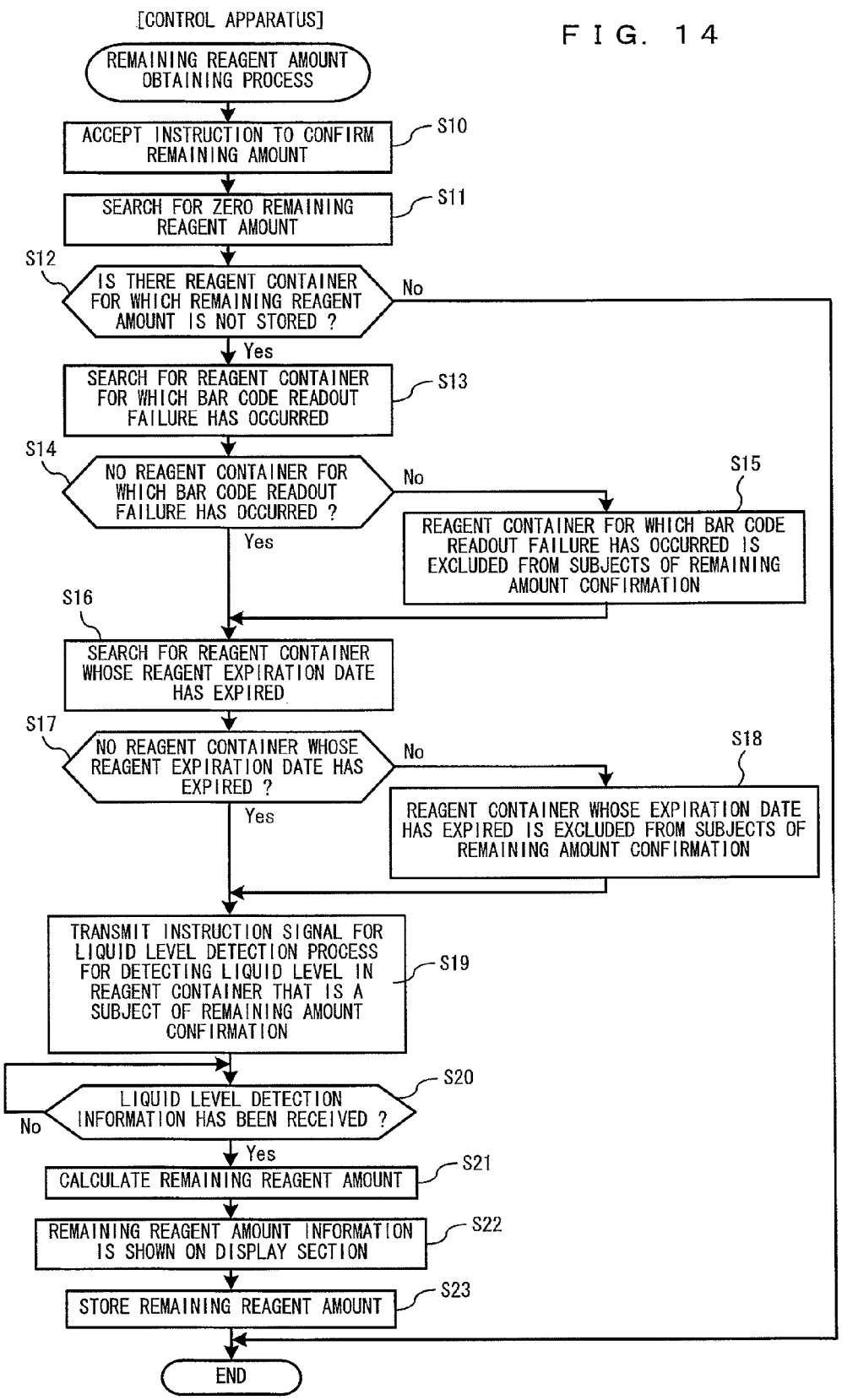
FIG. 14 is a flowchart showing a remaining reagent amount obtaining process of the embodiment.

FIG. 14 is a flowchart showing the remaining reagent amount obtaining process of the present embodiment. First, at step S10, an instruction to confirm reagent amounts remaining in the reagent containers 300 placed in the reagent storing section 6 is accepted. This instruction is provided when the user directly touches with a finger, or clicks with a mouse, the "REMAINING AMOUNT CONFIRMATION" button 601 shown in the reagent information list display screen 450 displayed on the display section 4b of the control apparatus 4.

Subsequently, the control section 4a determines whether or not there is, among the reagent containers placed in the reagent storing section 6, a reagent container for which the remaining reagent amount information is not stored in the hard disk 401d. To be specific, at step S11, the control section 4a uses the remaining reagent amount information as a key to searching the reagent information database 36 stored in the hard disk 401d for a reagent container for which a "-(hyphen)" is stored in the fields of the remaining reagent amount information (the fields of "usable amount" and "number of remaining tests"). Then, at step S12, when the control section 4a determines that there is no reagent container for which the remaining reagent amount information is not stored, that is, when there is no reagent container for which a "-(hyphen)" is stored in the fields of the remaining reagent amount information in the reagent information database 36 (determination "No"), the remaining reagent amount obtaining process ends here. On the other hand, when the control section 4a determines that there is a reagent container for which the remaining reagent amount information is not stored, that is, when there is a reagent container for which a "-(hyphen)" is stored in the fields of the remaining reagent amount information of the reagent information database 36 (determination "Yes"), the processing proceeds to step S13. Then at step S13, a reagent container, for which a bar code readout failure has occurred, is searched for. To be specific, the control section 4a uses lot numbers and container types as keys to searching the reagent information database 36 stored in the hard disk 401d for a reagent container for which at least one of the lot number and the container type has not been determined, from among reagent containers for which a "-(hyphen)" is stored in the fields of the remaining reagent amount information.

Then, at step S14, the control section 4a determines whether or not there is a reagent container for which a bar code readout failure has occurred. When the control section 4a determines that there is a reagent container for which a bar code readout failure has occurred (determination "No"), the processing proceeds to step S15. At step S15, the reagent container for which the bar code readout failure has been determined is excluded from the subjects of confirmation of the remaining reagent amount. Then, the processing proceeds to step S16. On the other hand, when the control section 4a determines at step S14 that there is no reagent container for which a bar code readout failure has occurred (determination "Yes"), the processing proceeds to step S16. At step S16, a reagent container whose reagent expiration date has expired is searched for. To be specific, the control section 4a uses expiration dates in the reagent information database 36 stored in the hard disk 401d, as keys to searching for a reagent container whose expiration date has expired, from among reagent containers that are the subjects of confirmation of the remaining reagent amount.

Next, at step S17, the control section 4a determines whether or not there is a reagent container that contains a reagent whose expiration date has expired. When the control section 4a determines that there is a reagent container that contains a reagent whose expiration date has expired (determination "No"), the reagent container whose reagent expiration date has expired is excluded, at step S18, from the subjects of confirmation of the remaining reagent amount. Then, the processing proceeds to step S19. On the other hand, when the control section 4a determines at step S17 that there is no reagent container whose reagent expiration date has expired (determination "Yes"), the control section 4a transmits, at step S19 to the control section 501 of the measurement mechanism section 2, an instruction signal for the liquid level detection process for detecting the liquid level in each reagent container that is a subject of confirmation of the remaining reagent amount.

<Liquid Level Detection Process>

Figure 15:
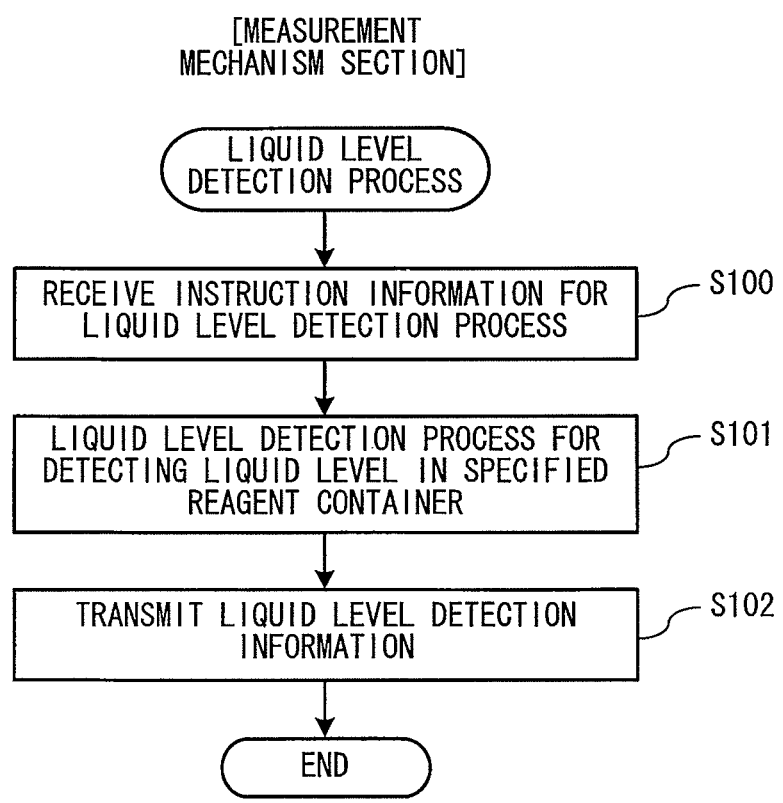
FIG. 15 is a flowchart showing a liquid level detection process performed by the measurement mechanism section.

FIG. 15 is a flowchart showing the liquid level detection process performed by the measurement mechanism section 2. First, at step S100, the control section 501 of the measurement mechanism section 2 receives the instruction signal for the liquid level detection process, which is transmitted from the control section 4a. Next, at step S101, the liquid level detection process is performed for detecting the liquid level in each specified reagent container. In the present embodiment, a liquid level detection operation for detecting a reagent liquid level is performed using the liquid level sensor S1 provided at the tip of the pipette part 121 of the reagent dispensing arm 120 and using the liquid level sensor S2 provided at the tip of the pipette part of the sample dispensing arm 70. That is, the liquid level detection is performed using both the pipette parts alternately.

Figure 16:
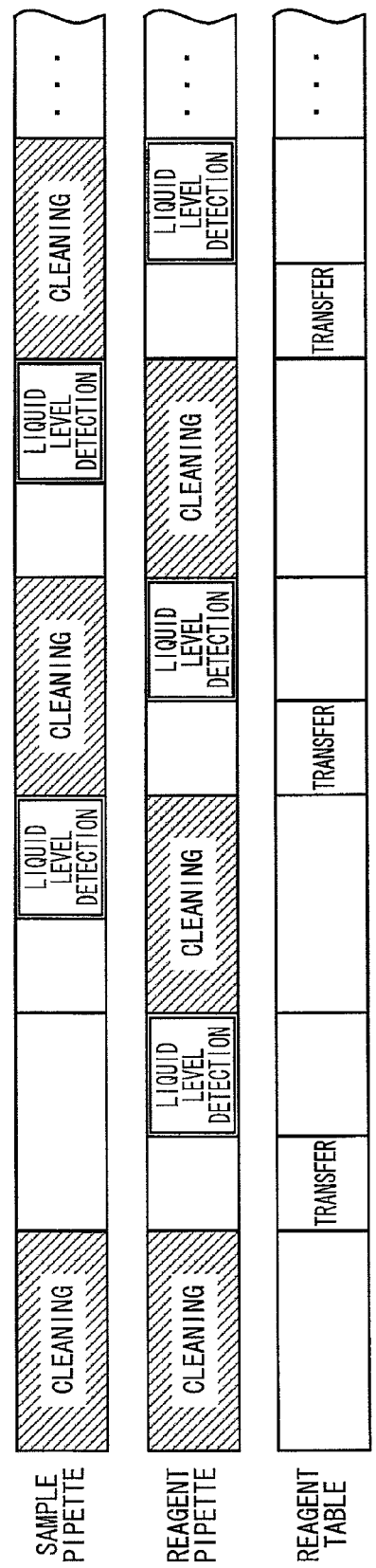
FIG. 16 shows a timetable for liquid level detection that is performed using a reagent pipette and a sample pipette alternately.

FIG. 16 shows a timetable for the liquid level detection that is performed using the pipette part 121 (reagent pipette) of the reagent dispensing arm 120 and the pipette part (sample pipette) of the sample dispensing arm 70 alternately. In this example, first, both the pipettes are cleaned prior to the liquid level detection. Then, a reagent table moves such that a reagent container that is to be subjected to the liquid level detection first is disposed in a reagent aspirating position of the reagent pipette. When the reagent table has moved to dispose the reagent container in the reagent aspirating position, the reagent pipette performs the liquid level detection process.

When the liquid level detection process by the reagent pipette ends, the reagent table moves such that a reagent container that is to be subjected to the liquid level detection second is disposed in a reagent aspirating position of the sample pipette. At the same time as the reagent table moves, the reagent pipette is cleaned. When the reagent table has moved to dispose the reagent container in the reagent aspirating position, the liquid level detection process by the sample pipette is performed.

When the liquid level detection process by the sample pipette ends, the reagent table moves such that a reagent container that is to be subjected to the liquid level detection third is disposed in the reagent aspirating position of the reagent pipette. At the same time as the reagent table moves, the sample pipette is cleaned. When the reagent table has moved to dispose the reagent container in the aspirating position, the liquid level detection process by the reagent pipette is performed again. Thereafter, the same operations are repeated until the liquid level detection process has been performed for all the specified reagent containers. Thus, by performing the reagent liquid level detection using both the reagent pipette and the sample pipette, the time required for the liquid level detection can be reduced.

Next, at step S102, pieces of liquid level detection information obtained from the above operations are sequentially transmitted to the control section 4a of the control apparatus 4 from the control section 501 of the measurement mechanism section 2.

Return to FIG. 14, at step S20, the control section 4a determines whether or not the liquid level detection information has been received from the control section 501. When the control section 4a determines that the liquid level detection information has been received from the control section 501 (determination "Yes"), the processing proceeds to step S21. Then, at step S21, the control section 4a calculates remaining reagent amounts.

Figure 17:
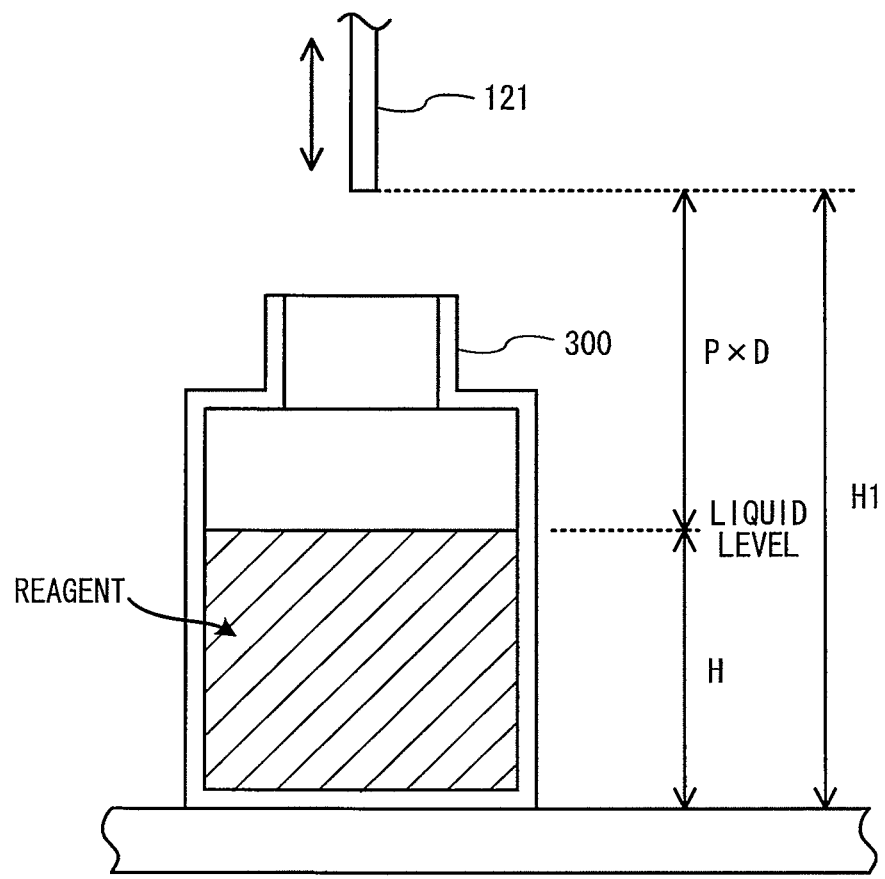
FIG. 17 illustrates a method for calculating a remaining reagent amount based on the liquid level detection.

FIG. 17 illustrates a method for calculating a remaining reagent amount based on the liquid level detection. Although FIG. 17 shows the pipette part 121 of the reagent dispensing arm 120, the remaining reagent amount can also be calculated using the pipette part of the sample dispensing arm 70 based on the same principle. The pipette part 121 moves downward from an initial position (height H1) that is set for a reagent aspirating operation. The pipette part 121 is driven by a stepping motor which is not shown, and is configured to move by a distance D each time one pulse is inputted to the stepping motor. When the liquid level sensor S1 provided at the tip of the pipette part 121 has reached and contacted the surface of a reagent, the surface of the reagent is detected, and also, the number of pulses P, which is one type of liquid level detection information obtained when the liquid level sensor S1 detects the surface of the reagent, is obtained. The height H1 and the distance D are prestored in the hard disk 401d of the control section 4a.

Subsequently, based on the obtained number of pulses P and the stored height H1 and distance D, the control section 4a calculates a height H of the liquid level of the reagent, using an equation (1) below.

$$H = H1 - P \times D \tag{1}$$

Then, based on the height H of the reagent liquid level, which is obtained from the equation (1), and based on an inner area S of the reagent container, which is prestored in the hard disk 401d of the control section 4a, the control section 4a calculates a remaining amount T of the reagent by using an equation (2) below.

$$T = H \times S \tag{2}$$

Figure 21:
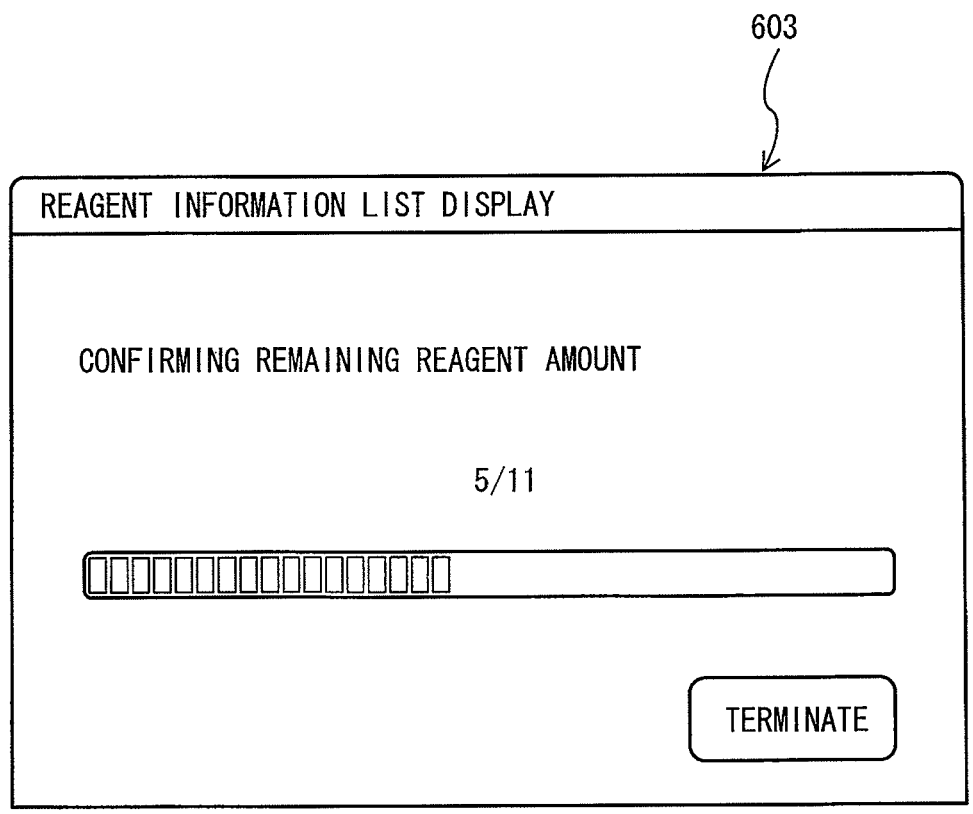
FIG. 21 shows a remaining amount confirmation window.

FIG. 21 shows a remaining amount confirmation window 603 which indicates that a remaining reagent amount confirmation process is being performed. The window 603 is displayed on the display section 4b when the remaining reagent amount obtaining process is being performed. The window 603 herein indicates that the remaining amount has been confirmed for five types of reagents from among 11 types of reagents that are the subjects of the confirmation.

Next, at step S22, the remaining reagent amount information calculated at step S21 is shown on the display section 4b of the control apparatus 4. Further, at step S23, the remaining reagent amount information calculated at step S21 is stored in the reagent information database 36 of the hard disk 401d of the control section 4a.

<Reagent Replacement Process>

Figure 22:
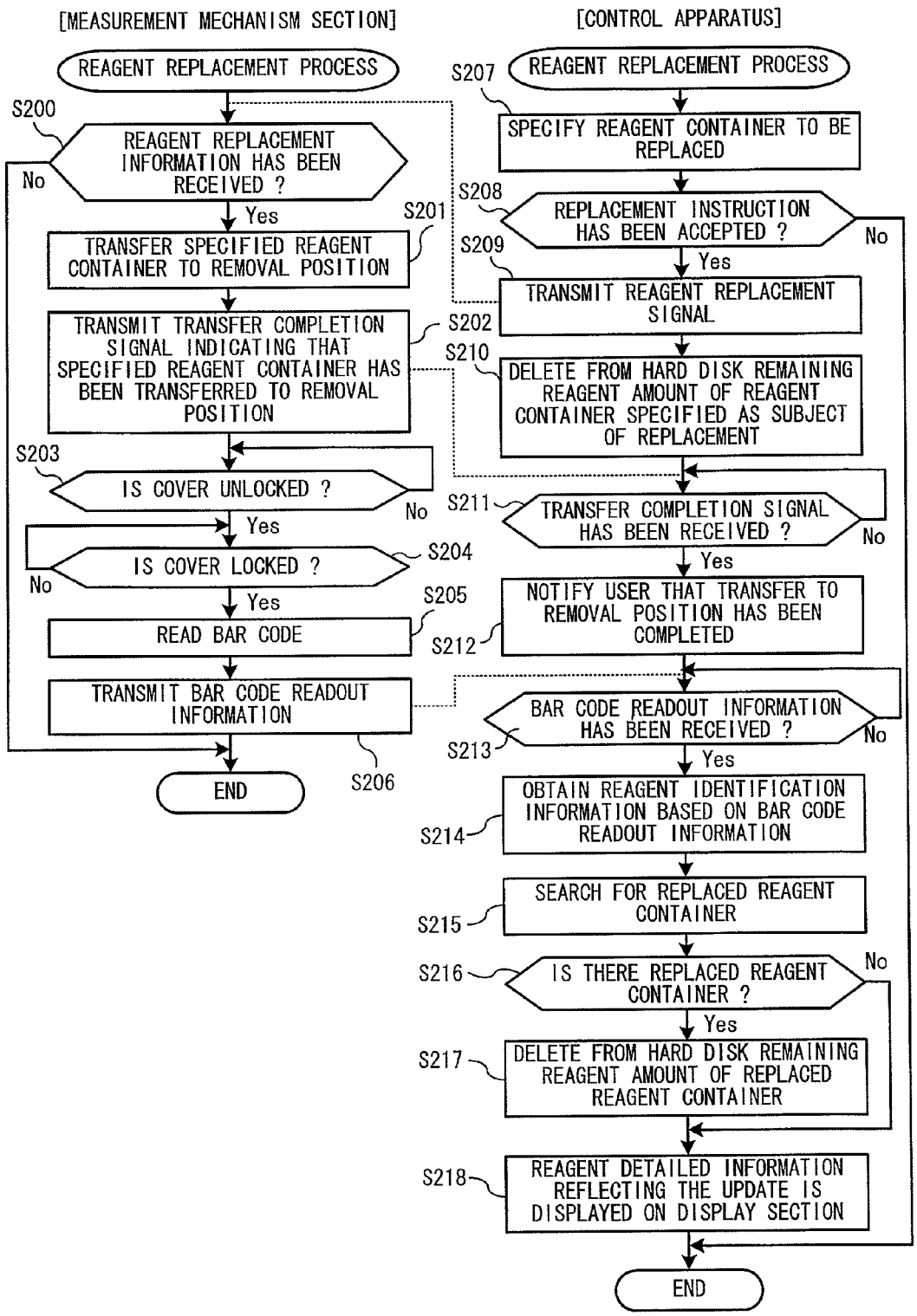
FIG. 22 is a flowchart illustrating operations, performed when reagent replacement is performed, to delete remaining reagent amount information from a memory.

FIG. 22 is a flowchart illustrating a reagent replacement process. Hereinafter, the reagent replacement process will be described with reference to FIG. 22.

First, at step S207, the user specifies a reagent container to be replaced. This specification can be performed on the reagent management screen 410 by directly touching, or clicking, a reagent indicium corresponding to the reagent container to be replaced. Subsequently, at step S208, the control section 4a of the control apparatus 4 determines whether or not a reagent replacement instruction has been accepted. The user can provide this instruction by directly touching, or clicking, the "REPLACE/ADD REAGENT" button 440a on the reagent management screen 410. When the control section 4a determines that the reagent replacement instruction has been accepted (determination "Yes"), the processing proceeds to step S209. At step S209, a reagent replacement signal is transmitted from the control section 4a to the control section 501 of the measurement mechanism section 2. On the other hand, when the control section 4a does not determine that the reagent replacement instruction has been accepted (determination "No"), the reagent replacement process ends.

At step S200, the control section 501 of the measurement mechanism section 2 determines whether or not the reagent replacement signal has been received from the control section 4a. When the control section 501 determines that the reagent replacement signal has been received (determination "Yes"), the processing proceeds to step S201. At step S201, the specified reagent container is transferred to a removal position. To be specific, through controlling of the first drive section 502 or second drive section 503 by the control section 501, a reagent table holding the reagent to be replaced rotates such that a first reagent container rack 310 or a second reagent container rack 320, which is holding the specified reagent container, is transferred to the removal position (below the first cover 30 or the second cover 40).

When the reagent container rack holding the specified reagent container is transferred to the removal position, a transfer completion signal indicating that the reagent container rack holding the specified reagent container has been transferred to the removal position, is transmitted from the control section 501 to the control section 4a at step S202. Note that, the control section 501 is able to, by counting the number of pulses of a drive pulse signal supplied to the first drive section 502 or to the second drive section 503, determine the amount of rotational movement of the first reagent table 11 or the second reagent table 12 from its original position. Accordingly, based on the amount of movement from the original position, the control section 501 can recognize that the first reagent table 11 or the second reagent table 12 has moved to transfer the rack holding the specified reagent container to the removal position. Based on this recognition, the control section 501 generates the transfer completion signal.

When the transfer completion signal is transmitted from the control section 501 to the control section 4a, the control section 4a determines at step S211 whether or not the transfer completion signal has been received. When it is determined at step S211 that the transfer completion signal has been received (determination "Yes"), the user is notified, at step S212, that the reagent container rack holding the specified reagent container has been transferred to the removal position. To be specific, the notification is performed by changing, in the reagent management screen, the color of the specified reagent container into a predetermined color (e.g., green). Also, when the reagent container rack holding the specified reagent container has been transferred to the removal position, the LED indicator 51 or 52 previously illuminating in red during the transferring of the reagent container rack illuminates in blue in the reagent replacement section 7. In this manner, the user is notified that the reagent container rack holding the specified reagent container has been transferred to the removal position.

Next, in order to perform reagent replacement work, the user unlocks the lock mechanism of the cover of the table that is the subject of the reagent replacement. Then, at step S203, the control section 501 determines whether or not the lock of the cover has been unlocked. Note that, in the reagent replacement work performed by the user, after the user removes the first cover 30 or the second cover 40 whose lock state is unlocked, the user holds the grip portion (313 or 327) of the reagent container rack in the removal position (below the first cover 30 or the second cover 40), and takes out the reagent container rack. Then, the user replaces the specified reagent container 300 with a reagent container 300 containing a new reagent. Thereafter, the reagent container rack on which the replacing reagent is placed is returned to the removal position. Next, the user attaches the first cover 30 or the second cover 40 to the reagent container rack, and locks the cover. Subsequently, a lock detector of the cover transmits a lock signal to the control section 501. Then, at step S204, the control section 501 determines whether or not the cover has been locked.

When the control section 501 determines at step S204 that the first cover 30 or the second cover 40 has been locked (determination "Yes"), a bar code reading operation is performed at step S205. In the bar code reading operation, the control section 501 controls the first reagent table 11 or the second reagent table 12 and also controls the reagent bar code reader 350, in order to read the bar code of the first reagent container rack 310 or the second reagent container rack 320, on which the replacing reagent is placed, and read the bar codes of all the reagent containers 300 held by the first reagent container rack 310 or the second reagent container rack 320, on which the replacing reagent is placed. Positional information that is obtained as a result of reading the barcodes, and reagent information or container absence information which corresponds to the positional information (holder numbers), are sent to the control section 501 and then stored in the RAM 501c.

Next, at step S206, the control section 501 transmits, to the control section 4a, the read bar code information (bar code readout information) stored in the RAM 501c. When the bar code readout information is transmitted from the control section 501 to the control section 4a, the control section 4a determines at step S213 whether or not the bar code readout information has been received. When it is determined at step S213 that the bar code readout information has been received (determination "Yes"), reagent identification information, such as the reagent name, container type, lot number, expiration date, and the like, is obtained at step S214 based on the bar code readout information, for all the reagents in the reagent rack holding the replacing reagent.

Subsequently, at step S215, the control section 4a searches for the reagent container that has been replaced. To be specific, the control section 4a searches for a reagent container of which the reagent identification information obtained at step S214 does not coincide with any piece of reagent identification information stored in the reagent information database 36. Then, at step S216, the control section 4a determines whether or not there exists a reagent container that has been replaced. When it is determined that there exists a reagent container that has been replaced (determination "Yes"), the remaining reagent amount information about the replaced reagent container is deleted at step S217 from the reagent information database 36 stored in the hard disk 401d of the control section 4a. Note that, in the reagent replacement, since the entire rack, which holds the reagent container specified as a subject of the replacement, is removed from the reagent storing section 6, there is a case where other reagent containers are also replaced in addition to the reagent container specified as a subject of the replacement. Therefore, it is also determined at step S216 whether or not other reagent containers have also been replaced in addition to the reagent container specified as a subject of the replacement. Then, at step S218, the control section 4a updates the information in the reagent information database 36, accordingly, and reagent detailed information that reflects the update is displayed on the reagent management screen.

Figure 23:
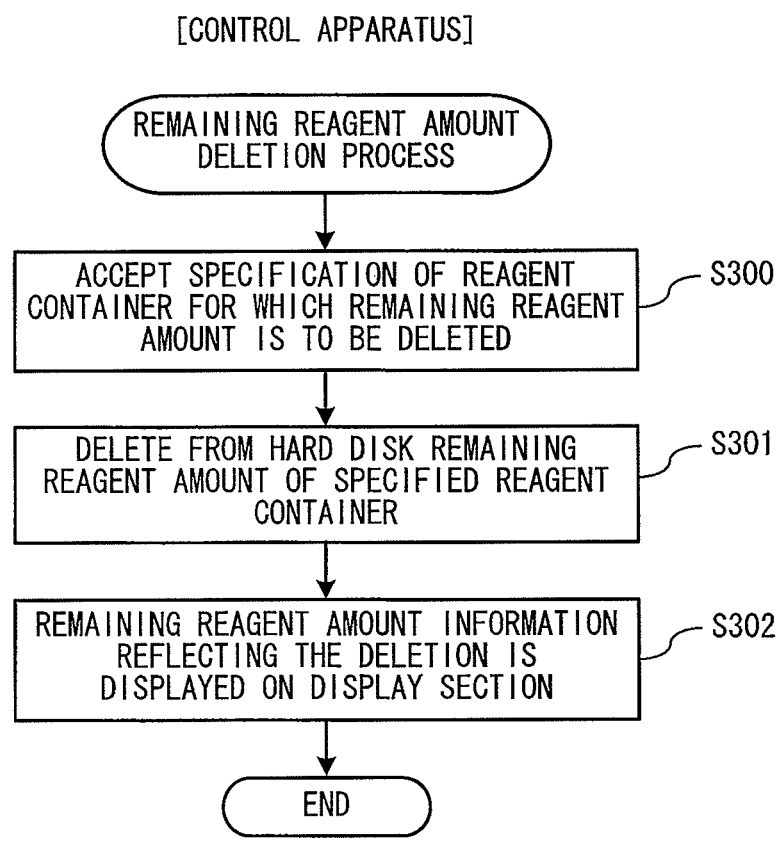

Note that, the sample analyzer 1 of the present embodiment is configured to be able to delete, in response to an instruction from the user, the remaining reagent amount of a reagent container specified by the user. For example, if, when a rack is removed from the reagent storing section 6, a reagent container is replenished with the same reagent as that previously contained in the reagent container without being replaced with a new reagent container, the remaining reagent amount in the reagent container changes. In such a case, as shown in FIG. 23, the user specifies, on the reagent management screen 410, a reagent indicium corresponding to the reagent container having been replenished with the reagent, and then presses or clicks the "REAGENT REPLACEMENT COMPLETED" button 431. As a result, the specification of the reagent container for which the remaining reagent amount is to be deleted, is accepted at step S300. Then, at step S301, the specified remaining reagent amount information about the specified reagent container is deleted from the reagent information database 36 stored in the hard disk 401d of the control section 4a. Next, at step S302, the remaining reagent amount information reflecting the deletion is displayed on the reagent management screen 410.

<Measurement Start Signal Transmission Process (Warning for Insufficient Remaining Reagent Amount)>

Figure 24:
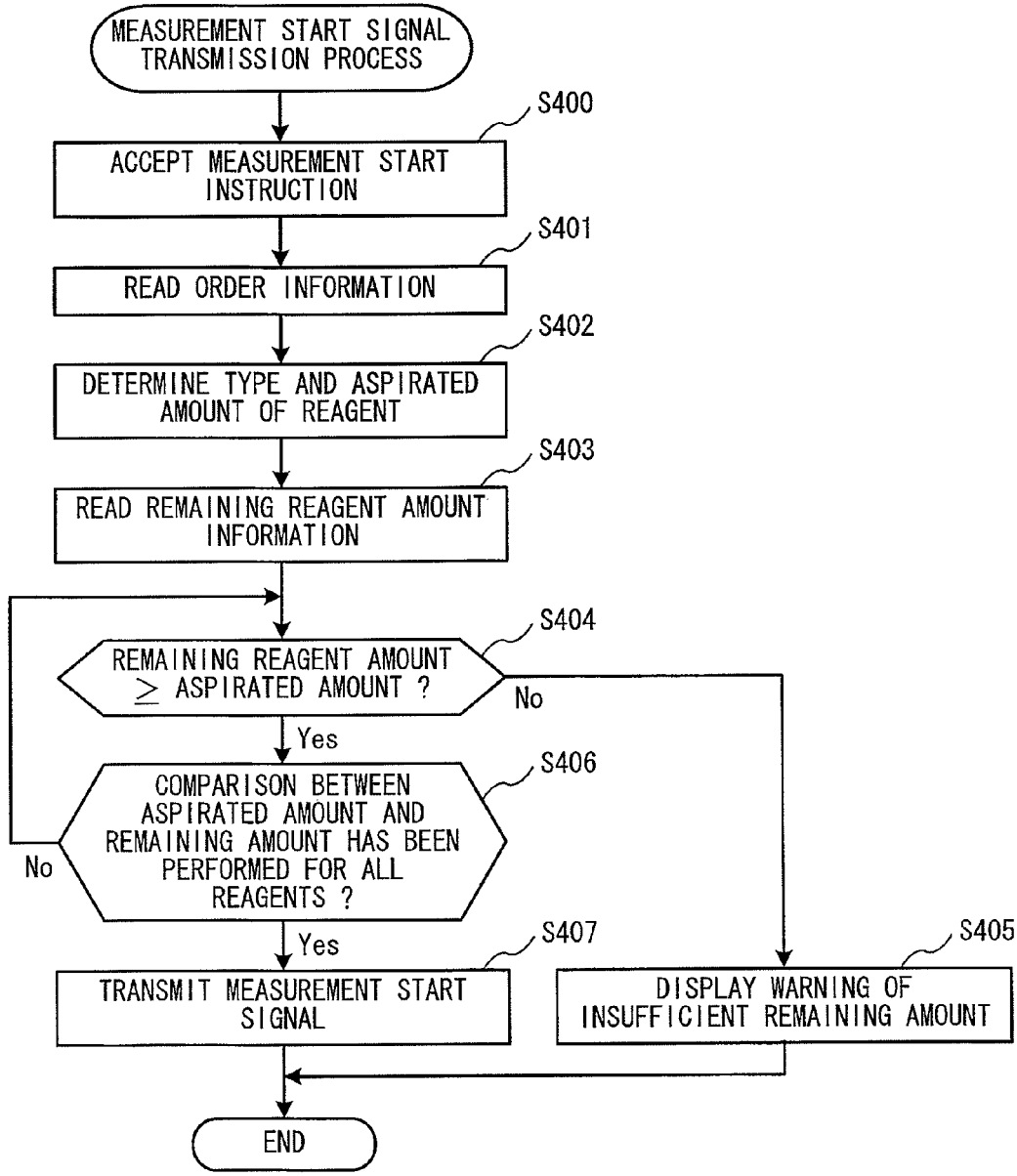
FIG. 24 is a flowchart illustrating operations to determine, prior to the start of a measurement operation, whether or not a remaining reagent amount is insufficient.

Described next with reference to FIG. 24 is a process which the control section 4a of the control apparatus 4 performs when transmitting, to the measurement mechanism section 2, the measurement start signal for providing an instruction to start the measurement. Here, before transmitting the measurement start signal to the measurement mechanism section 2, the control section 4a determines whether or not a necessary amount of reagent for the measurement is left. If the remaining amount is less than the necessary amount, the control section 4a performs a process of displaying a warning.

First, when an instruction to start a measurement operation is accepted at step S400 as a result of the user having pressed the start button on the menu screen, the control section 4a of the control apparatus 4 reads, at step S401 from the hard disk 401d, order information about the measurement for which the measurement start instruction has been accepted. The order information is inputted by the user via the keyboard 4c of the control apparatus 4. The order information contains an ID number, a measurement type, and the like of each sample to be measured. The hard disk 401d of the control section 4a stores a map or table that shows correspondence relationships among measurement types, reagent types used for the respective measurement types, and reagent amounts used for the respective measurement types.

Then, at step S402, a type and amount (to-be-aspirated amount) of reagents to be used in the measurement are determined by the control section 4a, based on the read order information and the map or table. Next, at step S403, the remaining reagent amount information about the reagents to be used in the measurement is read by the control section 4a from the reagent information database 36 stored in the hard disk 401d.

Subsequently, at step S404, the control section 4a determines whether or not the remaining reagent amount read at step S403 is equal to or greater than the to-be-aspirated amount determined at step S402. When determining that the remaining reagent amount is equal to or greater than the to-be-aspirated amount (determination "Yes"), the control section 4a proceeds to a process at step S406. On the other hand, when determining that the remaining reagent amount is less than the to-be-aspirated amount (determination "No"), the control section 4a proceeds to a process at step S405. At step S405, the control section 4a displays, on the reagent management screen 410, a warning that the remaining reagent amount is insufficient.

At step S406, the control section 4a determines whether or not the comparison between the to-be-aspirated amount and the remaining amount has been performed for all the reagents of the type and amount determined at step S402. When the control section 4a determines at step S406 that the comparison between the to-be-aspirated amount and the remaining amount has not been performed for all the reagents (determination "No"), the processing returns to step S404. Then, in the same manner as described above, the determination as to whether or not the remaining reagent amount is equal to or greater than the to-be-aspirated amount is performed.

On the other hand, when the control section 4a determines at step S406 that the comparison between the to-be-aspirated amount and the remaining amount has been performed for all the reagents of the type and amount specified at step S402 (determination "Yes"), the control section 4a transmits a measurement start signal to the control section 501 of the measurement mechanism section 2 at step S407.

In the present embodiment, the remaining reagent amount confirmation process is performed when the user's instruction to perform the remaining reagent amount confirmation is accepted. Alternatively, the remaining reagent amount confirmation process can be performed as apart of the initializing process of the sample analyzer, which includes initializing of programs.

Figure 25:
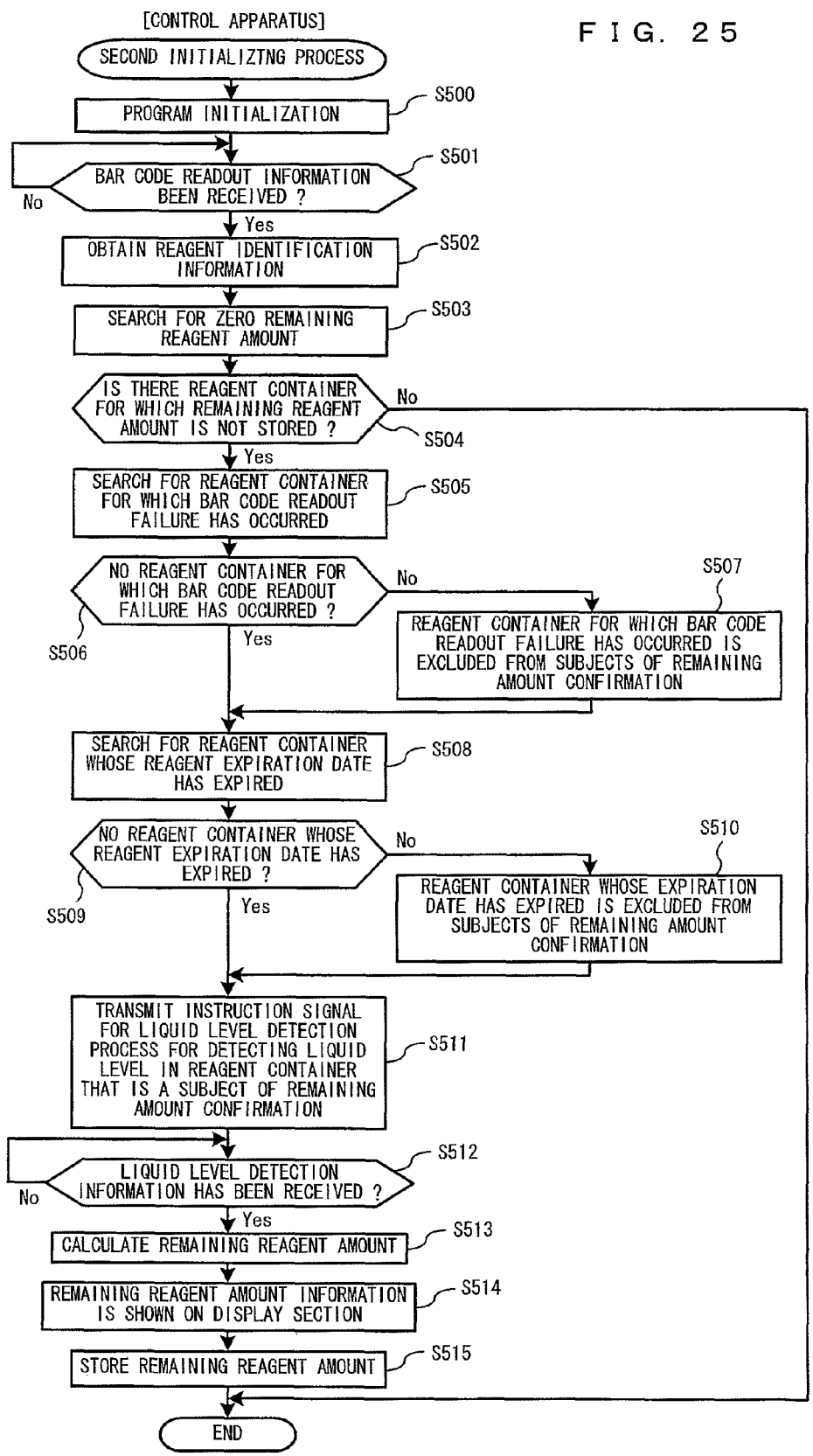
FIG. 25 is a flowchart showing a variation of the remaining reagent amount obtaining process.

FIG. 25 is a flowchart showing a variation of the remaining reagent amount obtaining process. Similarly to the flowchart shown in FIG. 13, programs stored in the control section 4a of the control apparatus 4 are initialized at step S500 when the control apparatus 4 is turned on. Subsequently, at step S501, the control section 4a of the control apparatus 4 determines whether or not bar code readout information obtained by the measurement mechanism section 2 has been received. When the control section 4a determines that the bar code readout information has been received, the processing proceeds to step S502. At step S502, "reagent identification information", that is, information indicating what reagents are placed in which positions on the reagent tables, is obtained based on the bar code readout information. The obtained reagent identification information is stored in the reagent information database 36.

Then, after the "reagent identification information" is obtained, the remaining reagent amount obtaining process is performed at steps S503 to S515 by the same operations as those performed at steps S11 to S23 of FIG. 14.

Thus, in the remaining reagent amount obtaining process of the above variation, after the sample analyzer is turned on and the bar code reading operation is performed by the reagent bar code reader 350, the remaining reagent amount obtaining process is automatically performed, even without an instruction from the user, for reagent containers of which the remaining reagent amount is unknown. Therefore, it is possible to certainly recognize, prior to the start of the measurement, a reagent whose remaining amount is highly likely to become insufficient during the measurement operation, and to prepare for the replacement in advance.

Note that, in the remaining reagent amount obtaining process of the above variation, the remaining reagent amount of each reagent container placed in the reagent storing section 6 is automatically obtained after the sample analyzer is turned on and the bar code reading operation is performed by the reagent bar code reader 350. However, the present invention is not limited thereto. For example, when the sample analyzer is turned on and starts up, the remaining reagent amount of each reagent container placed in the reagent storing section 6 may be automatically obtained, and the bar code reading operation by the reagent bar code reader 350 may be performed thereafter. Also in this manner, it is possible to certainly recognize, prior to the start of the measurement, a reagent whose remaining amount is highly likely to become insufficient during the measurement operation, and to prepare for the replacement in advance.

In another example, when a rack holding reagent containers having replaced old containers during the reagent replacement process is returned to the reagent storing section 6, the remaining reagent amount of each replacing reagent container may be automatically obtained after the bar codes of the rack and the reagent containers held by the rack are read. In this manner, the remaining reagent amount of each replacing reagent container can be assuredly recognized even without the user's instruction to perform the remaining amount confirmation.

In the present embodiment, a plurality of reagent containers are circumferentially placed on the round-shaped first reagent table 11 and on the annular-shaped second reagent table 12. The first reagent table 11 and the second reagent table 12 are each rotatable in both the clockwise direction and the counterclockwise direction. Also, these tables are configured to be rotatable independently from each other. Therefore, it is difficult for the user to recognize what reagents are placed in which positions on the reagent tables. It is also difficult to recognize remaining amounts of multiple reagents on the reagent tables. However, according to the present invention, it is possible to certainly recognize, prior to the start of the measurement, a reagent whose remaining amount is highly likely to become insufficient during the measurement operation, and to prepare for the replacement in advance. The present invention is advantageous in this respect.

Figure 26:
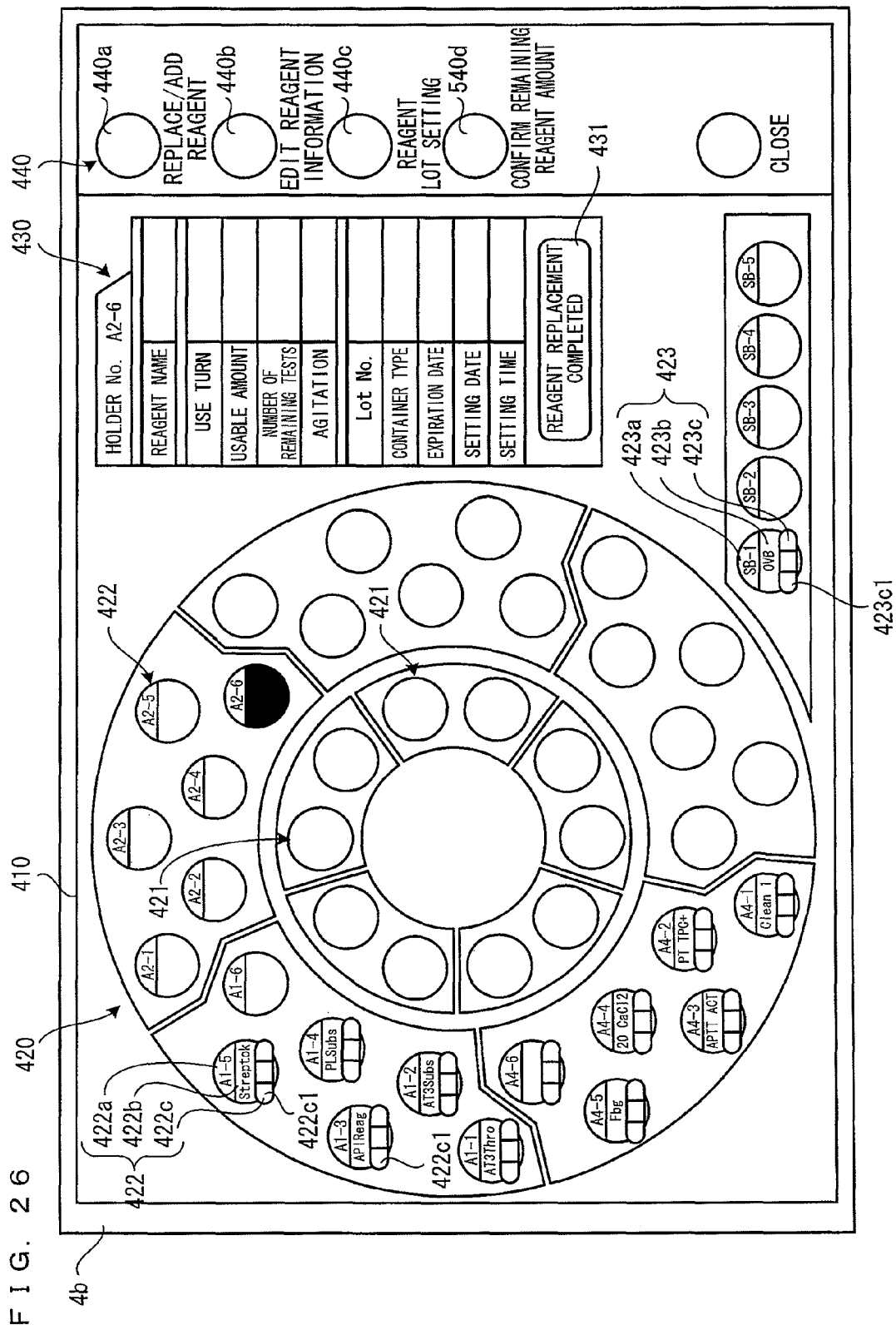
FIG. 26 shows a variation of the reagent management screen displayed on the display section of the control apparatus.

Further, in the present embodiment, the "REMAINING AMOUNT CONFIRMATION" button 601 for providing an instruction to start the remaining reagent amount obtaining process is provided on the lower right side of the reagent information list display screen 450 (a screen that is displayed when the reagent information list button 440*d* on the reagent management screen 410 is pressed). However, as shown in FIG. 26, a "REMAINING REAGENT AMOUNT CONFIRMATION" button 540*d* for providing an instruction to start the remaining reagent amount obtaining process may be provided within the operation means display area in the reagent management screen.

Still further, in the present embodiment, in the reagent replacement process, a reagent container that has been replaced is searched for based on the bar code readout information. If there is a reagent container that has been replaced, the remaining reagent amount information about the replaced reagent container is deleted from the reagent information database 36. However, the present invention is not limited thereto. For example, when the user designates a reagent container to be replaced, by pressing the "REPLACE/ADD REAGENT" button 440*a*, the remaining reagent amount information about the reagent container specified by the user may be deleted from the reagent information database 36.

Still further, in the present embodiment, a sensor for liquid level detection is provided at the tip of the reagent dispensing pipette and at the tip of the sample dispensing pipette. However, both the pipettes may be formed from an electrically conductive material, and these pipettes may each function as an electrically conductive component. In this case, there is no necessity to provide the sensor as a separate component. Accordingly, the total number of components can be reduced.

Although the degree of remaining reagent amount is indicated by coloring or uncoloring the three areas 422*c*1, the number of areas is not limited to 3. Further, the degree of remaining reagent amount can be indicated by changing a kind of color used in the coloring, for example, among green, yellow, and red. Also, the coloring may be shown as blinking so as to provide a warning.

Still further, in the present embodiment, the liquid level of a reagent in a reagent container is detected, and the remaining amount of the reagent in the reagent container is obtained based on a result of the detection. However, the present invention is not limited thereto. For example, the weight of the reagent container may be measured by a weight sensor, and the remaining amount of the reagent in the reagent container may be calculated based on the obtained weight data.

Still further, in the present embodiment, the control section 4*a* of the control apparatus 4 is configured to be able to accept an instruction to start the remaining reagent amount obtaining process, which is provided through the "REMAINING AMOUNT CONFIRMATION" button 601, during a period from when the above-described initializing process of the control apparatus 4 has ended until when the measurement start signal is transmitted to the measurement mechanism section 2, and also during a period from when the measurement operation by the measurement mechanism section 2 has ended until when the measurement start signal providing an instruction to start the next measurement is transmitted to the measurement mechanism section 2. The control section 4*a* is also configured not to accept an instruction to start the remaining reagent amount obtaining process, which is provided through the "REMAINING AMOUNT CONFIRMATION" button 601, during a period from when the measurement start signal has been transmitted to the measurement mechanism section 2 until when the measurement operation of the measurement mechanism section 2 ends. However, the present invention is not limited thereto.

For example, the control section 4*a* may be configured to be able to accept an instruction to start the remaining reagent amount obtaining process, which is provided through the "REMAINING AMOUNT CONFIRMATION" button 601, during a period from when the measurement start signal has been transmitted to the measurement mechanism section 2 until when the dispensing operations by the reagent dispensing arm 120 and the sample dispensing arm 70 start, in addition to a period from when the above-described initializing process of the control apparatus 4 has ended until when the measurement start signal is transmitted to the measurement mechanism section 2 and a period from when the measurement operation of the measurement mechanism section 2 has ended until when the measurement start signal providing an instruction to start the next measurement is transmitted to the measurement mechanism section 2. Also, the control section 4*a* may be configured not to accept an instruction to start the remaining reagent amount obtaining process, which is provided through the "REMAINING AMOUNT CONFIRMATION" button 601, during a period from when the dispensing operations by the reagent dispensing arm 120 and the sample dispensing arm 70 have started until when the measurement operation by the measurement mechanism section 2 ends.

Still further, the control section 4*a* may be configured to be able to always accept an instruction to start the remaining reagent amount obtaining process, which is provided through the "REMAINING AMOUNT CONFIRMATION" button 601, during a period from when the above-described initializing process of the control apparatus 4 has ended until when the control apparatus 4 is shut down. In this case, a pipette dedicated for detection of the liquid level in a reagent container may be provided in addition to the reagent dispensing pipette and the sample dispensing pipette. Also, when an instruction to start the remaining reagent amount obtaining process is accepted during the measurement operation performed by the measurement mechanism section 2, a reservation of the remaining reagent amount obtaining process may be accepted. Then, after the measurement operation has ended, the remaining reagent amount obtaining process may be started.

Still further, the control section 4*a* may be configured to be able to accept an instruction to start the remaining reagent amount obtaining process, which is provided through the "REMAINING AMOUNT CONFIRMATION" button 601, during a period from when the above-described initializing process of the control apparatus 4 has ended until when an input, by the user, of order information is accepted, and also during a period from when the measurement operation by the measurement mechanism section 2 has ended until when an input of order information is accepted for the next measurement. The control section 4a may also be configured not to accept an instruction to start the remaining reagent amount obtaining process, which is provided through the "REMAINING AMOUNT CONFIRMATION" button 601, during a period from when an input of order information has been accepted until when the measurement operation by the measurement mechanism section 2 ends.

Still further, the control section 4a may be configured to be able to accept an instruction to start the remaining reagent amount obtaining process, which is provided through the "REMAINING AMOUNT CONFIRMATION" button 601, during a period from when the above-described initializing process of the control apparatus 4 has ended until when the measurement start signal is transmitted to the measurement mechanism section 2, and during a period from when the measurement operation by the measurement mechanism section 2 has ended until when the measurement start signal providing an instruction to start the next measurement is transmitted to the measurement mechanism section 2, except for a period from when an instruction to perform reagent replacement has been accepted until when the reagent replacement process is completed. The control section 4a may also be configured not to accept an instruction to start the remaining reagent amount obtaining process, which is provided through the "REMAINING AMOUNT CONFIRMATION" button 601, during a period from when the measurement start signal has been transmitted to the measurement mechanism section 2 until when the measurement operation by the measurement mechanism section 2 is completed, and also during a period from when an instruction to perform reagent replacement has been accepted until when the reagent replacement process is completed.

What is claimed is:

1. A sample analyzer comprising:
   a reagent container holder for holding a plurality of reagent containers, wherein each reagent container is configured to contain a reagent;
   an identification information obtainer for obtaining identification information of one or more reagent containers held by the reagent container holder;
   a memory for storing a reagent information database including identification information obtained by the identification obtainer and a reagent amount information indicating a remaining amount of a reagent in a reagent container held by the reagent container holder;
   a reagent dispenser comprising a reagent aspirating pipette for aspirating a reagent in a reagent container held by the reagent container holder, and a driving mechanism for moving the reagent aspirating pipette;
   a liquid level sensor for detecting a liquid level of a reagent in a reagent container held by the reagent container holder based on a contact of the reagent aspirating pipette with the reagent in the reagent container;
   a detection section for measuring a measurement sample prepared from a sample and a reagent dispensed by the reagent dispenser; and
   a controller configured to perform operations comprising:
      receiving a first instruction to obtain reagent amount information;
      in response to receiving the first instruction, determining one or more reagent containers of the plurality of reagent containers whose reagent amount information is not stored in the memory by searching the reagent information database;
      controlling the reagent dispenser to insert the reagent aspirating pipette into only the one or more determined reagent containers to detect, by the liquid level sensor, a corresponding liquid level of the reagent in each of the determined reagent containers;
      storing, in the memory, the corresponding reagent amount information obtained by the liquid level sensor for each of the determined reagent containers;
      receiving a second instruction to start a sample analysis; and
      in response to the second instruction, determining a reagent used for a sample analysis related to the second instruction and controlling the reagent dispenser to insert the reagent aspiration pipette into a reagent container which contains the determined reagent to dispense the determined reagent.

2. The sample analyzer of claim 1, wherein the controller is further configured to,
   in response to the second instruction, control the liquid level sensor to detect a liquid level of the reagent used for the sample analysis related to the second instruction when aspirating the reagent by the reagent aspirating pipette.

3. The sample analyzer of claim 1, wherein the controller is further configured to,
   when the controller has determined a plurality of reagent containers whose reagent amount information is not stored in the memory, control the reagent dispenser to sequentially insert the reagent aspirating pipette into the determined plurality of reagent containers to detect, by the liquid level sensor, a corresponding liquid level in each of the determined plurality of reagent containers.

4. The sample analyzer of claim 3, further comprising a display, wherein
   the controller is further configured to control the display to display reagent amount information of all of the determined reagent containers.

5. The sample analyzer of claim 1, further comprising
   a display, wherein
   the controller is further configured to control the display to display a screen showing a button which is operable by a user, and
   receive the first instruction when the button has been operated by the user.

6. The sample analyzer of claim 1, further comprising:
   a display;
   a display controller for controlling the display so as to display a screen showing the remaining reagent amount information; and
   a replacement instruction receiver for receiving a replacement instruction to replace the reagent container held by the reagent container holder, wherein
   the display controller deletes, from the screen, the remaining reagent amount information of the reagent container for which the replacement instruction receiver has received the replacement instruction.

7. The sample analyzer of claim 1, further comprising:
   a display;
   a display controller for controlling the display so as to display a screen showing the remaining reagent amount information; and
   a determiner for determining whether another reagent container different from the reagent container is newly held by the reagent container holder, based on the identification information obtained by the identification information obtainer, wherein
   the display controller deletes, from the screen, the remaining reagent amount information of the reagent container, instead of which the determiner has determined that the another reagent container is newly held by the reagent container holder.

8. The sample analyzer of claim 1, further comprising a display, wherein the controller is further configured to control the display to display a screen showing the remaining reagent amount information stored in the memory, and when receiving specification of a reagent container for which a reagent amount information is to be deleted, the controller controls the display to delete from the screen, the remaining reagent amount information of the specified reagent container.

9. The sample analyzer of claim 1, further comprising a sample dispenser comprising a sample aspirating pipette for aspirating a sample, and a second driving mechanism for moving the sample aspirating pipette; and a second liquid level sensor for detecting a liquid level of a reagent in a reagent container held by the reagent container holder based on a contact of the sample aspiration pipette with the reagent in the reagent container, wherein the controller is further configured to, in response to the first instruction, control the sample dispenser to insert the sample aspirating pipette into a reagent container the reagent amount information of which is not stored in the memory to detect, by the second liquid level sensor, a liquid level of a reagent in the reagent container.

10. The sample analyzer of claim 9, further comprising a cleaner for cleaning the reagent aspirating pipette and the sample aspirating pipette, wherein the controller is further configured to control the cleaner and one of the reagent dispenser and the sample dispenser so as to clean the one of the reagent aspirating pipette and the sample aspirating pipette while the other of the reagent aspirating pipette and the sample aspirating pipette is performing a liquid level detection operation.

11. The sample analyzer of claim 1, wherein the controller is further configured to:

obtain order information that contains an analysis item for the sample;

determine whether a necessary amount of a reagent remains for performing analysis of the sample, based on a remaining reagent amount information of the reagent stored in the memory and the obtained order information; and provide a warning when the necessary amount of the reagent does not remain for performing the analysis of the sample.

12. The sample analyzer of claim 1, wherein the reagent contained in the reagent container held by the reagent container holder is a reagent which has been defrosted after having been stored in a frozen state.

13. The sample analyzer of claim 1, wherein the reagent contained in the reagent container held by the reagent container holder is a reagent which is obtained by dissolving freeze-dried reagent powder in purified water.

14. The sample analyzer of claim 1, wherein the reagent container holder comprises:

a round-shaped first table which is configured to be rotatable; and an annular-shaped second table which is configured to be rotatable independently from the first table and which is provided outside the first table so as to be concentric with respect to the first table, and wherein each of the first and second tables includes a plurality of reagent container holding areas circumferentially.

15. The sample analyzer of claim 1, wherein the first instruction is generated in response to a user input.

* * * * *